United States Patent
Schnorr

(10) Patent No.: US 10,646,156 B1
(45) Date of Patent: *May 12, 2020

(54) ADAPTIVE IMAGE PROCESSING IN ASSISTED REPRODUCTIVE IMAGING MODALITIES

(71) Applicant: Cycle Clarity, LLC, Awendaw, SC (US)

(72) Inventor: John Anthony Schnorr, Awendaw, SC (US)

(73) Assignee: Cycle Clarity, LLC, Awendaw, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/442,418

(22) Filed: Jun. 14, 2019

(51) Int. Cl.
| | |
|---|---|
| A61B 5/00 | (2006.01) |
| G16H 30/40 | (2018.01) |
| G16H 50/20 | (2018.01) |
| G16H 10/60 | (2018.01) |
| G06N 20/10 | (2019.01) |
| G06K 9/00 | (2006.01) |

(Continued)

(52) U.S. Cl.
CPC ........ *A61B 5/4325* (2013.01); *G06K 9/00671* (2013.01); *G06N 3/08* (2013.01); *G06N 20/10* (2019.01); *G06T 7/0012* (2013.01); *G16H 10/60* (2018.01); *G16H 30/40* (2018.01); *G16H 50/20* (2018.01)

(58) Field of Classification Search
CPC ........ G16H 30/40; G16H 50/20; G06N 20/10; G06N 3/02–088; A61B 5/4325
See application file for complete search history.

(56) References Cited

U.S. PATENT DOCUMENTS

| | | |
|---|---|---|
| 7,427,271 B2 | 9/2008 | Kirsner |
| 9,679,375 B2 | 6/2017 | Eskandari et al. |

(Continued)

FOREIGN PATENT DOCUMENTS

| | | |
|---|---|---|
| EP | 3363368 A1 | 8/2018 |
| WO | 2018080120 A1 | 5/2018 |

(Continued)

OTHER PUBLICATIONS

Parekh, Aarti M. et al.; Classification of Ovarian Cyst Using Soft computing technique; 2017; IEEE; 8th ICCCNT 2017, Delhi, India; 5 pages. (Year: 2017).*

(Continued)

*Primary Examiner* — Stanley K. Hill
(74) *Attorney, Agent, or Firm* — Gregory Finch; Finch Paolino, LLC

(57) ABSTRACT

Adaptive image processing, image analysis, pattern recognition, and time-to-event prediction in various imaging modalities associated with assisted reproductive technology. The reference image may be processed according to one or more adaptive processing frameworks for de-speckling or noise processing of ultrasound images. The subject image is processed according to various computer vision techniques for object detection, recognition, annotation, segmentation, and classification of reproductive anatomy, such as follicles, ovaries and the uterus. An image processing framework may also analyze secondary data along with subject image data to analyze time-to-event progression of the subject image.

20 Claims, 15 Drawing Sheets

(51) Int. Cl.
*G06N 3/08* (2006.01)
*G06T 7/00* (2017.01)

(56) References Cited

U.S. PATENT DOCUMENTS

| | | | |
|---|---|---|---|
| 9,773,325 | B2 | 9/2017 | Plakas et al. |
| 10,127,664 | B2 | 11/2018 | Govindjee et al. |
| 2018/0144471 | A1* | 5/2018 | Govindjee ............ G06T 7/0014 |
| 2018/0199815 | A1 | 7/2018 | Redei |

FOREIGN PATENT DOCUMENTS

| | | |
|---|---|---|
| WO | 2018222006 A1 | 12/2018 |
| WO | 201909919 A1 | 1/2019 |

OTHER PUBLICATIONS

Sonigo, Charlotte et al.; High-throughput ovarian follicle counting by an innovative deep learning approach; Scientific Reports (2018) 8:13499; pp. 1-9. (Year: 2018).*

Raine-Fenning, Nick et al.; Timing of oocyte maturation and egg collection during controlled ovarian stimulation: a randomized controlled trial evaluating manual and automated measurements of follicle diameter; 2010; Elsevier; Fertility and Sterility vol. 94, No. 1; pp. 184-188. (Year: 2010).*

Rodriguez-Fuentes, Adela et al.; Prospective evaluation of automated follicle monitoring in 58 in vitro fertilization cycles: follicular volume as a new indicator of oocyte maturity; 2010; Elsevier; Fertility and Sterility vol. 93, No. 2; pp. 616-620. (Year: 2010).*

Hiremath, P.S. et al., "Automatic Detection of Follicles in Ultrasound Images of Ovaries using Active Contours Method." 2010 IEEE International Conference on Computational Intelligence and Computing Research. Dec. 2010.

Chen, Terrence et al., "Automatic ovarian follicle quantification from 3D ultrasound data using global/local context with database guided segmentation." pp. 795-802. 2009 IEEE 12th International Conference on Computer Vision (ICCV). Sep. 2009.

Potocnik, B., et al., "Computerized detection and recognition of follicles in ovarian ultrasound images: a review." Med. Biol Eng Comput (2012) 50:1201-1212. Sep. 26, 2012. Springer-Verlag.

Güvenir, H.A., et al., "Estimating the chance of success in IVF treatment using a ranking algorithm." Med Biol Eng Comput 53:911-920. 2015. Online publication Apr. 17, 2015.

Vandekerckhove, Frank, et al. "The value of automated follicle volume measurements in IVF/ICSI." Frontiers in Surgery vol. 1, Article 18 (2014): 1-12.

Nilsson, Lars, et al. "Simplification of the method of in Vitro Fertilization: Sonographic Measurements of Follicular Diameter as the Sole Index of Follicular Maturity." Journal of In Vitro Fertilization and Embryo Transfer vol. 2, No. 1 (1985): 17-22.

* cited by examiner

ADAPTIVE IMAGE PROCESSING IN ASSISTED REPRODUCTIVE IMAGING MODALITIES

FIELD

The present disclosure relates to the field of digital image processing and digital data processing systems, and corresponding image data processing frameworks; in particular, an adaptive digital image processing framework for use in assisted reproductive technology (ART).

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

In general, infertility is defined as not being able to get pregnant (conceive) after one year (or longer) of unprotected sex. In vitro fertilization (IVF) is a medical treatment option for a significant population of couples experiencing infertility. Infertility can arise from a combination of disorders including male factor causes and female causes with tubal blockage, decreased egg number, decreased egg quality, ovulatory disorders, endometriosis, pelvic adhesions, and unexplained causes. The most aggressive form of treatment of infertility is called assisted reproductive technology (ART) which specifically means technology in which ova (i.e., egg cells) are extracted from the woman's ovaries, fertilized outside of the body, and the resultant embryo is transferred back into the uterus of the patient. The goal of ART is to identify the best embryo or embryos and return it to the patient's womb. A fundamental part of success in ART is creating the best quality eggs possible for an individual patient. The quality and maturity of the eggs is directly predictive for the likelihood the eggs fertilize to become embryos and for the quality of the embryos. The quality of the resultant embryo is predictive for the implantation rate which is defined as (the pregnancy per one embryo transfer) and the overall pregnancy rate (if a multiple embryo transfer is performed). The thickness and developmental pattern for the endometrium (the inner lining of the uterus and location for embryo implantation) is also predictive of implantation and pregnancy rates.

Ovarian follicles contain oocytes which are surrounded by granulosa cells. There are four different types of follicles at distinct stages of development: primordial, primary, secondary and tertiary (or antral). The number of primordial follicles, which is the true ovarian reserve, is determined in the fetus and declines throughout a woman's life. Primordial follicles consist of a dormant single layer of granulosa cells surrounding an oocyte. They are quiescent, but initiate growth depending on a sensitive balance between the factors that promote proliferation and apoptosis (i.e., cell death). When changing to primary follicles, the granulosa cells start to duplicate and become cuboidal. A glycoprotein polymer capsule, the zona pellucida, forms around the oocyte, separating it from the granulosa cells. When becoming secondary follicles, stroma-like theca-cells that surround the outer layer of the follicle undergo cytodifferentiation to become theca externa and theca interna, which are separated by a network of capillary vessels. The formation of a fluid-filled cavity adjacent to the oocyte, the antrum, defines the tertiary, or antral, follicle. Since there is no test available to evaluate the true ovarian reserve, ovarian antral follicle count (AFC) is accepted as a good surrogate marker. Ovarian antral follicles can be identified and counted using transvaginal ultrasound (US). AFC is frequently assessed in women of reproductive age, for various reasons including predicting the risk of menopause, suspicion of ovulatory dysfunction secondary to hyperandrogenism anovulation, and work-ups for infertility and assisted reproduction techniques.

Ultrasound (US) imaging has become an indispensable tool in the assessment and management of infertility for women undergoing ART. Decreased ovarian reserve and ovarian dysfunction are a primary cause for infertility, and the ovary is the most frequently ultrasound-scanned organ in an infertile woman. The first step in an infertility evaluation is the determination of ovarian status, ovarian reserve and subsequent follicle monitoring. Ovarian antral follicles can be identified and manually counted using transvaginal US. The antral follicles become more easily identifiable by US when they reach 2 millimeter (mm) in diameter, coinciding with the attainment of increased sensitivity to follicle-stimulating hormone (FSH). Antral follicles measuring between 2 and 10 mm are "recruitable," while antral follicles greater than 10 mm are usually referred to as "dominant" follicles. Infertility can also be associated with the growth of a dominant follicle beyond a preovulatory diameter and subsequent formation of a large anovulatory follicle cyst. The ovary is imaged for its morphology (e.g., normal, polycystic, or multicystic), for its abnormalities (e.g., cysta, dermoids, endometriomas, tumors, etc.), for its follicular growth in ovulation monitoring, and for evidence of ovulation and corpus luteum formation and function. Ovulation scans enable the physician to determine accurately the number of recruitable eggs, each individual follicle's egg maturity, and the appropriate timing of ovulation. In general, during infertility treatment, frequent two-dimensional (2D) US scans are done to visualize the growing follicles, and measurements are made of all follicles in the ovary (customarily 15 to 20 follicles) to determine the average follicular size of each follicle. This is performed 4 to 6 times during the 10 days while a patient is on medications (e.g., gonadotropin therapy). The typical time required to perform the ultrasound is approximately 10 to 15 minutes per patient plus additional time to enter the data into an electronic medical record (EMR) system (approximately 5 minutes) or electronic health record system (HER). Ovaries are classified into three types based on the number and size of the follicles. A cystic ovary is one containing one to two follicles measuring greater than 28 mm in diameter. A polycystic ovary is one containing twelve or more follicles measuring less than 10 mm. An ovary containing one to ten antral follicles measuring 2-10 mm and one or more antral follicles measuring 10-28 mm size, the "dominant" follicles, F is considered a normal ovary.

Current 2D US measurements of the follicles are made under the assumption that they are round, but frequently the follicles are irregularly shaped, making the measurements inaccurate. There is also significant human variability in measuring millimeter dimension objects by US, further complicating the accuracy of using this modality for follicle monitoring. It is also difficult to identify all of the follicles in the ovary using 2D US, leading to frequently missed measurements. The last complexity, but not the least, is the inter-observer follicle size measurement variabilities of ultrasonographers which requires further scrutiny by physicians during review. With the advent of three-dimensional (3D) ultrasound, resolution has steadily improved along with data connectivity. 3D ultrasound measurements of the ovary are performed by simply placing the probe in the vagina, directing it to the ovary, and pushing a button. 3D-US imaging has the advantage of a shorter examination time, as it enables storage of acquired data for offline analysis, and better inter-observer reliability. However, new features such as automated volume calculation (SonoAVC; GE Medical Systems) technique can incorrectly identify adjacent follicles and extraovarian tissue as being only one follicle. Despite improvements, there is no consensus on the best US technique with which to perform follicle counting. All semi-automated methods currently available have pros and cons and are affected by the operator's preference and skill, which are prone to inaccuracies and variability.

From a digital data processing systems perspective, the follicles are the regions of interest (ROIs) in an ovarian ultrasound image and can be detected using image processing techniques. The basic image processing steps, namely, pre-processing, segmentation, feature extraction and classification, can be applied to this complex task of accurate follicle recognition. However, imaging modalities that form images with coherent energy, such as US, suffer from speckle noise, which can impair the performance for automated operations such as computer aided diagnostics (CAD), a system that can, for example, differentiate benign and malignant lesion tissues for cancer diagnosis. CAD, in the context of ART, is desirable to address the tedious and time-consuming nature of manual follicle segmentation, sizing, counting, and ovarian classification, where accuracy requires operator skills and medical expertise. In the image classification process, a task is to specify the presence or absence of an object; the task of counting the objects also requires reasoning to ascertain the number of instances of an object present in a scene.

Speckle (acoustic interference) refers to the inherent granular appearance within tissues that results from interactions of the acoustic beam with small-scale interfaces that are about the size of a wavelength or smaller. These non-specular reflectors scatter the beam in all directions. Scatterings from these individual small interfaces combine through an interference pattern to form the visualized granular appearance. Speckle appears as noise within the tissue, degrading spatial and contrast resolution but also giving tissues their characteristic image texture. The speckle characteristics are dependent on the properties of the imaging system (e.g., ultrasound frequency, beam shape) and the tissue's properties (e.g., scattering object size distribution, acoustic impedance differences). Speckle is a form of locally correlated multiplicative noise, which may severely impair the performance of automatic operations like classification and segmentation, aimed at extracting valuable information for the end user. A number of approaches have been proposed to suppress speckle while preserving relevant image features. Most of these approaches rely on detailed classical statistical models of signal and speckle, either in the original or in a transform domain. The need exists for alternative methods to improve US resolution for improving AFC accuracy and CAD for ART.

The emerging field of machine learning (ML), especially deep learning, has made a significant impact on medical imaging modalities. Deep learning (DL) is a new form of ML that has dramatically improved the performance of machine learning tasks. DL uses artificial neural networks (ANNs), which consist of multiple layers of interconnected linear or non-linear mathematical transformations that are applied to the data with the goal to solve a problem such as object classification. The level of DL performance is greater than classical ML and does not require a human to identify and compute the critical features. Instead, during training, DL algorithms "learn" discriminatory features that best predict the outcomes. The amount of human effort required to train DL systems is less because it requires no feature engineering, or computation. When it comes to the medical image analysis domain, the data sets are often inadequate to reach the full potential of DL. In the computer vision domain, transfer learning and fine tuning are often used to solve the problem of a small data set. In general, DL algorithms recognize the important features of images and properly give weight to these features by modulating their inner parameters to make predictions for new data, thus accomplishing identification, segmentation, classification, or grading, and demonstrating strong processing ability and intact information retention.

The superiority of CAD based on deep learning has recently been reported for a wide spectrum of diseases, including gastric cancer, diabetic retinopathy, cardiac arrhythmia, skin cancer, and colorectal polyp. A wide variety of image types were explored in these studies, including pathological slides, electrocardiograms, and radiological images. A well-trained algorithm for a specific disease can increase the accuracy of diagnosis and working efficiency of physicians or medical experts, liberating them from repetitive tasks, as well as enhancing diagnostic accuracy, especially in the presence of subtle pathological changes that cannot be detected by visual assessment. DL algorithms can be optimized through the tuning of hyperparameters such as learning rate, network architectures, and activation functions. CAD based on DL thus has the potential to improve the performance of ART.

Convolutional neural networks (CNNs) or ConvNets are DL network architectures that have recently been employed successfully for image segmentation, classification, object detection and recognition tasks, shattering performance benchmarks in many challenging applications. Medical image analysis applications have heavily relied on feature engineering approaches, where algorithm pipelines are used to explicitly delineate structures of interest using segmentation algorithms to measure predefined features of these structures that are believed to be predictive, and to use these features to train models that predict patient outcomes. In contrast, the feature learning paradigm of CNNs adaptively learns to transform images into highly predictive features for a specific learning objective. The images and patient labels are presented to a network composed of interconnected layers of convolutional filters that highlight important patterns in the images, and the filters and other parameters of the network are mathematically adapted to minimize prediction error. Feature learning avoids biased a priori definition of features and does not require the use of segmentation algorithms that are often confounded by artifacts.

A CNN is comprised of multiple layers with neurons that process portions of an input image. The outputs of these neurons are tiled to form an overlap, which provides a filtered representation of the original image. This process is repeated for each layer until the final output is reached, which is typically the probabilities of predicted classes. The training of a CNN requires many iterations to optimize network parameters. During each iteration, a batch of samples is chosen at random from the input training set and undergoes forward-propagation through the network layers. In order to achieve optimal results, parameters within the network are updated through back-propagation to minimize a cost function. Once trained, a network can be applied on new or unseen data to obtain predictions. The main advantages of CNNs are that features can be automatically learned from a training set without the need for expert knowledge or hard-coding. The extracted features are relatively robust to image transformations or variations. In the field of medical imaging, CNNs have been mainly utilized for detection, segmentation, and classification. These tasks make up part of the CAD process flow, and the effective feature extraction or phenotyping of patients from EMR is a key step for potential further applications of the technology, such as the successful performance of ART using DL techniques, which has not been contemplated to date among experts in the field.

Due to the sequential nature of EMR or EHR data, there have been recently multiple promising works studying clinical events as sequential data. Many of them were inspired by works in natural language modeling, since sentences can be easily modeled as sequences of signals. There is a growing interest in predicting treatment prescription and individual patient outcomes by extracting information from these data using advanced analytics approaches. In particular the recent success of DL in image and natural language processing has encouraged the application of these state-of-the-art techniques to modeling clinical data as well. CNNs, such as Recurrent Neural Networks (RNNs), which have proven to be powerful in language modeling and machine translation, are more frequently applied to medical event data for predictive purposes, since natural language and medical records share the same sequential nature. DL and more specifically RNN have not been contemplated for use in improving the performance of ART, leaving an opening for significant new improvements in the field of ART through application of these technologies, such as that embodied in the disclosure of the present application.

A fundamental component of performing ART requires the stimulation of the ovary to produce multiple eggs. In a natural cycle, a typical woman makes one egg per month alternating between the two ovaries. With ART, the administration of exogenous gonadotropins, principally follicle stimulating hormones (e.g., FSH), will encourage each ovary to make on average 10 to 15 eggs that grow in the fluid-filled ovarian follicle. As the follicles grow, they become progressively more dependent on gonadotropins for continued development and survival. FSH promotes granulosa cell proliferation and differentiation, allowing the follicle to increase in size. The follicles grow from their resting size of 3-7 mm to 20 mm in size over a 10-day medication treatment during which the dose is adjusted based upon ovarian response. During the 10 days of medications, US is performed 3 to 4 times to measure the follicular size and monitor the response. The size of the follicle predicts the likelihood there is an egg in the follicle, the quality of the egg, and the likelihood that the egg is mature.

A critical component of ART success is creating the best quality eggs possible for an individual patient. The quality and maturity of the eggs is directly predictive for the likelihood the eggs fertilize to become embryos and is predictive for the quality of the embryos. The quality of the resultant embryo is predictive for the implantation rate which is defined as (the pregnancy per one embryo transfer) and the overall pregnancy rate (if a multiple embryo transfer is performed). The numbers and quality of oocytes available are critical factors of the success rates for ART.

One of the challenges in patient care is that the eggs do not all start at the same size and grow at the same rate. Therefore, the follicles will vary in size at any one time during the stimulation period. The timing of a patient's egg retrieval (time-to-event) is therefore based on trying to determine when the majority of the follicles are mature in size. Sometimes that requires pushing the ovarian stimulation longer to effectively over stimulate some of the follicles with the goal of getting the majority of the follicles in the mature range. This follicle monitoring technique is performed with a combination of transvaginal US and blood measurements of estradiol and progesterone. The success of ART would benefit from the automated connection and coordination of ultrasound imaging, follicle monitoring, size determination, counting, determination of hormone levels and cycle days to important clinical time-to-events such as follicular maturity, egg maturity, number of embryos, blastocyst embryo development, and pregnancy rates. DL has the potential to improve ART where a sparsity of patient data exists for optimal timing of follicle extraction and implantation.

Survival analysis is about predicting the time duration until an event occurs. Traditional survival modeling assumes the time durations follow an unknown distribution. The Cox proportional hazard model is among the most popular of these models. The Cox model and its extensions are built on the proportional hazards hypothesis which assumes that the hazard ratio between two instances is constant in time and a risk prediction is based on a linear combination of covariates. However, there are too many complex interactions in real world clinical applications such as ART. A more comprehensive survival model is needed to better fit clinical data with nonlinear risk functions. In addition, a patient's EHR is longitudinal in nature because health conditions evolve over time. Therefore, temporal information is needed in order to apply CNN for analyzing patient EMR. DL of patient EMR or EHR has the potential to improve the determination of timing for follicle extraction and implantation.

The need exists for improving the performance of ART through an efficient management of IVF. Through applied effort, ingenuity, and innovation, Applicant has identified a number of deficiencies of the conventional approach, including but not limited to limitation of US modality, manual and inaccurate determination of AFC, identifying the quality and maturity of eggs, and the inability to synthesize patient health records, patient biomarker diagnostics, and treatment regimens for the intelligent determination of optimal follicle extraction timing to improve implantation and pregnancy rates. Applicant has developed a solution that is embodied by the present invention, which is described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Aspects of the present disclosure provide for an ensemble of Deep Learning (DL) systems and methods in the provision of assisted reproductive technology (ART) for the diagnosis, treatment, and clinical management of infertility. In various embodiments, the ensemble comprises the processing of at least one image containing one or more patient's reproductive anatomy from imaging modalities using at least one Artificial Neural Network (ANN). In various embodiments, the ensemble comprises object detection, recognition, annotation, segmentation, or classification of at least one image acquired from an imaging modality using at least one ANN. In various embodiments, the ensemble further comprises at least one detection framework for object detection, localization, and counting using at least one ANN. In various embodiments, the ensemble comprises feature extraction or phenotyping of one or more patients from an electronic health or medical record using at least one ANN. In various embodiments, the ensemble further comprises at least one framework for predicting time-to-event outcomes using at least one ANN. In various embodiments, the ANN includes, but is not limited to, a Convolution Neural Network (CNN), Recurrent Neural Network (RNN), Fully Convolutional Neural Network (FCNN), Dilated Residual Network (DRN), Generative Adversarial Networks (GANs), the like, or combinations thereof. The ensemble comprises serial or parallel combinations of ANNs as an artificial intelligent computer-aided diagnostic (CAD) and predictive system for the clinical management of infertility.

Aspects of the present disclosure provide for the said ANN system and method for pre-processing or processing one or more imaging modalities in the provision of ART for the diagnosis, treatment and clinical management of clinical infertility. In various embodiments, the imaging modality preferably comprises ultrasound, including but not limited to two-dimension (2D), three-dimension (3D), four-dimension (4D), Doppler, or the like. In various embodiments, the images comprise reproductive anatomy, including but not limited to a cell, fallopian tube, ovary, ovum, ova, follicle, cyst, uterus, uterine lining, endometrial thickness, uterine wall, eggs, blood vessels, or the like. In various embodiments, an image comprises one or more normal or abnormal morphology, texture, shape, size, color, or the like of said anatomy. In various embodiments, the image pre-processing comprises at least one de-speckling or denoising model for improving image quality to enhance image retrieval, interpretation, diagnosis, decision-making, or the like.

Aspects of the present disclosure provide for the said ANN system and method for object detection, recognition, annotation, segmentation, or classification of at least one US image in the provision of ART for the diagnosis, treatment and clinical management of clinical infertility. In various embodiments, said system and method enable the detection, recognition, annotation, segmentation, or classification of a(n) ovary, cyst, cystic ovary, polycystic ovary, follicle, antral follicle, or the like. In various embodiments, the ANN system and method include, but are not limited to, at least one of Convolution Neural Network (CNN), Recurrent Neural Network (RNN), Fully Convolutional Neural Network (FCNN), Dilated Residual Network (DRN), or Generative Adversarial Networks (GANs) architecture. In various embodiments, the architecture comprises at least one input, convolution, pooling, map, sampling, rectification (non-linear activation function), normalization, full connection (FC), or output layer. In various embodiments, the convolution method comprises the use of one or more patch, kernel, or filter relating to said reproductive anatomy. In various embodiments, the one or more said ANN are trained using one more optimization method. In various embodiments, the input layer of an alternative ANN comprises data derived from an output layer of said ANN. In various embodiments, one or more results of detection, recognition, annotation, segmentation, or classification from an output layer of said one or more ANN are recorded in at least one electronic health record database. In alternative embodiments, the said results are transmitted and stored within a database residing in a cloud-based server.

Aspects of the present disclosure provide for the said ANN system and method for an object detection framework in the provision of ART for the diagnosis, treatment and clinical management of clinical infertility. In various embodiments, the said system and method enables object detection, localization, counting, and tracking over time of one or more reproductive anatomy from one or more US images. In various embodiments, the reproductive anatomy includes but is not limited to a(n): ovary, cyst, cystic ovary, polycystic ovary, follicle, oocyte, antral follicle, fallopian tube, uterus, endometrial pattern, endometrial thickness, or the like. In various embodiments, the ANN system and method includes, but is not limited to, at least one Convolution Neural Network (CNN), Recurrent Neural Network (RNN), Fully Convolutional Neural Network (FCNN), Dilated Residual Network (DRN), or Generative Adversarial Networks (GANs) architecture. In various embodiments, the architecture comprises at least one input, convolution, pooling, map, sampling, rectification (non-linear activation function), normalization, full connection (FC), or output layer. In various embodiments, the convolution method comprises the use of one or more patch, kernel, or filter relating to said reproductive anatomy. In various embodiments, the one or more said ANN are trained using one or more optimization method. In various embodiments, the input layer of an alternative ANN comprises data derived from an output layer of said ANN. In various embodiments, one or more results of detection, localization, counting, and tracking from an output layer of said one or more ANN are recorded in at least one electronic health record database. In alternative embodiments, the said results are transmitted and stored within a database residing in a cloud-based server.

Aspects of the present disclosure include said ANN system and method for analyzing an electronic medical record in the provision of ART for the diagnosis, treatment and clinical management of clinical infertility. In various embodiments, said system and method enable feature extraction or phenotyping of one or more patients from at least one longitudinal patient electronic medical record (EMR), electronic health record (HER), database, or the like. In various embodiments, the said medical record comprises one or more stored patient record, preferably records of patients undergoing infertility treatment, ultrasound image, ultrasound manufacturer, ultrasound model, ultrasound probe, ultrasound frequency, images of said reproductive anatomy, patient age, patient ethnic background, patient demographics, physician notes, clinical notes, physician annotation, diagnostic results, body-fluid biomarkers, medication doses, days of medication treatment, hormone markers, hormone level, neohormones, endocabinoids, genomic biomarkers, proteomic biomarkers, Anti-Mullerian hormone, estradiol, estrone, progesterone, FSH, Lutinizing Hormone (LH), inhibins, renin, relaxin, VEGF, creatine kinase, hCG, fetoprotein, pregnancy-specific b-1-glycoprotein, pregnancy-associated plasma protein-A, placental protein-14, follistatin, IL-8, IL-6, vitellogenin, calbindin-D9k, therapeutic treatment, treatment schedule, implantation schedule, implantation rate, follicle size, follicle number, AFC, follicle growth rate, pregnancy rate, date and time of implantation (i.e., event), CPT code, HCPCS code, ICD code, or the like. In various embodiments, the one or more said medical record field is transformed into one or more temporal matrix, preferably with time as one dimension and a specific event as another dimension. In various embodiments, the said ANN architecture comprises at least one input, convolution, pooling, map, sampling, rectification (non-linear activation function), normalization, full connection (FC), prediction, or output layer. In various embodiments, the convolution method comprises the use of one or more patch, kernel, or filters relating to factors for predicting time for follicle extraction and implantation. In various embodiments, the one or more said ANN are trained using one or more optimization method. In various embodiments, the input layer of an alternative ANN comprises data derived from an output layer of said ANN. In various embodiments, one or more identified patient phenotype or predictive result from an output layer of said one or more ANN are recorded in at least one electronic health record database. In alternative embodiments, the said results are transmitted and stored within a database residing in a cloud-based server.

Aspects of the present disclosure provide for the said ANN system and method for predictive planning in the provision of ART for the diagnosis, treatment and clinical management of clinical infertility. In various embodiments, the ANN system and method comprise at least one framework for predicting time-to-event outcomes. In various embodiments, time-to-event outcomes include, but are not limited to, initiation-termination ovarian stimulation, number of cycle day, follicle retrieval, follicle recruitment, oocyte retrieval, follicle stage, follicle maturity, fertilization rate, blastocyst embryo development, embryo quality, implantation, or the like. In various embodiments, the said ANN architecture comprises at least one input, convolution, pooling, map, sampling, rectification (non-linear activation function), normalization, full connection (FC), Cox model, and output layer. In various embodiments, the convolution method comprises the use of one or more patch, kernel, or filters relating to factors for predicting time-to-event. In various embodiments, the one or more said ANN are trained using one or more optimization method. In various embodiments, the one or more said predictions are compared with patient outcomes to adaptively train one or more network weights of one or more interconnected layer. In various embodiments, the input layer of an alternative ANN comprises data derived from an output layer of said ANN. In various embodiments, one or more derived time-to-event result from an output layer of said one or more ANN are recorded in at least one electronic health record database. In alternative embodiments, the said results are transmitted and stored within a database residing in a cloud-based server.

Aspects of the present disclosure provide for a computer program product for use in the provision of ART for the diagnosis, treatment and clinical management of clinical infertility. In various embodiments, the product comprises a system and methods for collecting, processing, and synthesizing clinical insights from at least one patient data, US image from a US scanner/device, retrieved US image, patient medical record from an electronic medical record database, patient record relating to fertility, patient endocrinology record, patient clinical notes, physician clinical notes, data from database residing on said cloud-based server, results from one or more output layer of one or more said ANNs, and artificial intelligence engine. In various embodiments, the artificial intelligence engine incorporates one or more results from one or more said ANNs to generate one or more clinical insights. In various embodiments, the cloud-based server comprises one or more user applications in conjunction with one or more browser enabling a user to access clinical information, perform further data processing or analyses, and retrieve or receive one or more clinical insights. In various embodiments, a user accesses the said information using a mobile computing device or a desktop computing unit. In various embodiments, a mobile application enables the user to access information from said computer product.

Specific embodiments of the present disclosure provide for a computer-aided diagnostic and predictive system for the clinical management of infertility, the system comprising an imaging sensor operable to execute one or more imaging modalities to collect one or more images of a reproductive anatomy of a subject; a storage device for storing, locally or remotely, the one or more images of the reproductive anatomy of the subject; and, at least one processor operably engaged with at least one computer-readable storage medium storing computer-executable instructions thereon that, when executed, cause the processor to perform one or more actions, the one or more actions comprising receiving the one or more images of the reproductive anatomy of the subject; processing the one or more images of the reproductive anatomy of the subject to detect one or more reproductive anatomical structures and annotate one or more anatomical features of the one or more reproductive anatomical structures; comparing the one or more anatomical features to at least one linear or non-linear framework to predict at least one time-to-event outcome; and, generating at least one graphical user output corresponding to one or more clinical actions for the subject.

Further specific embodiments of the present disclosure provide for a computer-aided diagnostic and predictive system for the clinical management of infertility, the system comprising an imaging sensor operable to execute one or more imaging modalities to collect one or more images of a reproductive anatomy of a patient; an artificial intelligence engine configured to receive, locally or remotely, the one or more images of the reproductive anatomy of the patient, the artificial intelligence engine configured to process the one or more images of the reproductive anatomy of the patient and generate at least one time-to-event outcome prediction according to at least one linear or non-linear framework; an outcome database configured to communicate clinical outcome data to the artificial intelligence engine, the clinical outcome data being incorporated into the at least one linear or non-linear framework; an application server operably engaged with the artificial intelligence engine to receive the at least one time-to-event outcome prediction, the application server being configured to generate one or more recommended clinical actions for the clinical management of infertility in response to the at least one time-to-event outcome prediction; and, a client device being communicably engaged with the application server, the client device being configured to display a graphical user interface containing the one or more recommended clinical actions for the clinical management of infertility.

Still further specific embodiments of the present disclosure provide for at least one computer-readable storage medium storing computer-executable instructions that, when executed, perform a method for predicting a clinical outcome associated with the provision of an assisted reproductive technology, the method comprising receiving one or more digital images of a reproductive anatomy of a patient; processing the one or more digital images of the reproductive anatomy of the patient to detect one or more reproductive anatomical structures and annotate one or more anatomical features of the one or more reproductive anatomical structures; analyzing the one or more anatomical features according to at least one linear or non-linear framework; and, predicting at least one time-to-event outcome according to the at least one linear or non-linear framework.

Further aspects of the present disclosure provide for a method for processing digital images in assisted reproductive technologies, the method comprising obtaining one or more digital images of a reproductive anatomy of a patient through one or more imaging modalities; processing the one or more digital images to detect one or more reproductive anatomical structures; processing the one or more digital images to annotate, segment, or classify one or more anatomical features of the one or more reproductive anatomical structures; analyzing the one or more anatomical features according to at least one linear or non-linear framework; and, predicting at least one time-to-event outcome of an assisted reproductive procedure according to the at least one linear or non-linear framework.

Further aspects of the present disclosure provide for a method of image processing for clinical planning in assisted reproductive technologies, the method comprising receiving one or more digital images of a reproductive anatomy of a patient through one or more imaging modalities; processing the one or more digital images to detect one or more reproductive anatomical structures; processing the one or more digital images to annotate, segment, or classify one or more anatomical features of the one or more reproductive anatomical structures; analyzing the one or more anatomical features according to at least one linear or non-linear framework; predicting at least one time-to-event outcome of an assisted reproductive procedure according to the at least one linear or non-linear framework; and, generating one or more clinical recommendations associated with the assisted reproductive procedure.

Still further aspects of the present disclosure provide for method for clinical management of infertility, comprising obtaining ovarian ultrasound images of a subject's ovarian follicles using an ultrasound device; analyzing, according to at least one linear or non-linear framework, the ovarian ultrasound images to annotate, segment, or classify one or more anatomical features of the subject's ovarian follicles to predict a time-to-event outcome; and, generating one or more clinical recommendations for an assisted reproductive procedure.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which.

DETAILED DESCRIPTION

Figure 1:
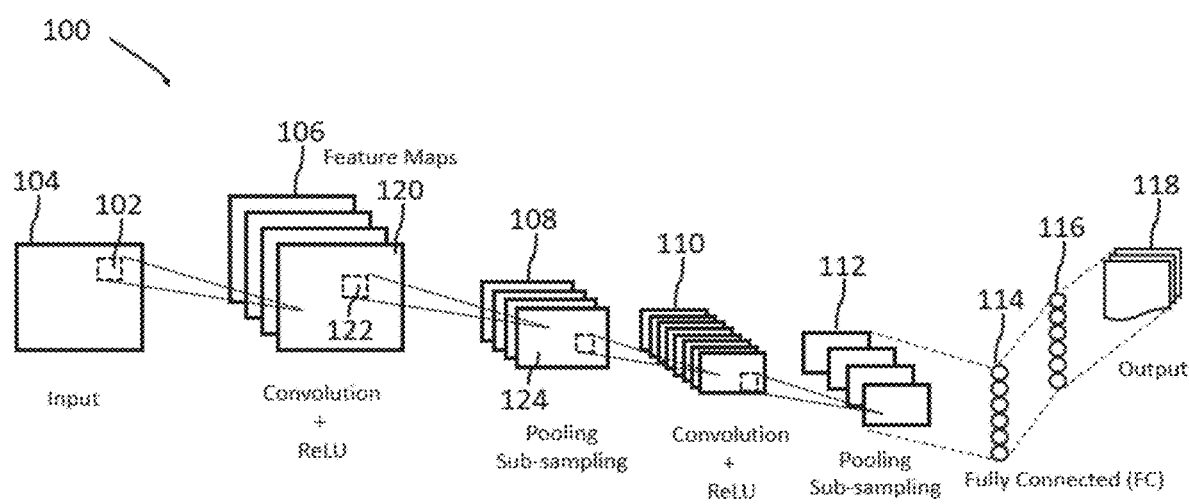
FIG. 1 is an illustration of the elements of a Convolutional Neural Network architecture, in accordance with an embodiment of the present disclosure.

Exemplary embodiments are described herein to provide a detailed description of the present disclosure. Variations of these embodiments will be apparent to those of skill in the art. Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Embodiments of the present disclosure provide for an ensemble of Deep Learning (DL) systems and methods in the provision of assisted reproductive technology (ART) for the diagnosis, treatment, and the clinical management of infertility. The ensemble comprises one or more artificial neural networks (ANNs) systems and methods for de-speckle or noise processing of ultrasound images, using computer vision techniques (e.g., Convolution Neural Networks) for object detection, recognition, annotation, segmentation, classification, counting, and tracking of reproductive anatomy, such as follicles and ovaries. ANNs systems and methods are also assembled to analyze electronic medical records to identify and phenotype characteristic time-to-event patient outcomes for predicting the timing of optimal follicle extraction and implantation in patients. The methods and systems are incorporated into a cloud-based computer program and mobile application that enable physician and patient access to clinical insights in the clinical and patient management of infertility.

FIG. 1 is an illustration 100 of the elements of a Convolutional Neural Network architecture. A convolutional neural network (CNN) is a special type of artificial neural network (ANN). The fundamental difference between a densely connected layer of an ANN and a convolution layer is that ANNs learn global patterns in their input feature space. In contrast, convolution layers learn local patterns that are usual small 2D windows, patches, filters, or kernels 102 of an input image (or input layer) 104. The patterns learned by CNNs are translational invariant, allowing global pattern recognition within an image or sequence. A CNN can also learn spatial hierarchies of patterns whereby a first convolution layer (or hidden layer) 106 can learn small local patterns such as edges and additional or subsequent layers will learn larger patterns comprising features of the previous or first layer.

A CNN learns highly non-linear mappings by interconnecting layers of artificial neurons arranged in many different layers with non-linear activation functions. A CNN architecture comprises one or more convolutional layers 106, 110 interspersed with one or more sub-sampling layers 108, 112 or non-linear layers, which are typically followed by one or more fully connected layers 114, 116. Each element of the CNN receives inputs from a set of features in the previous layer. The CNN learns concurrently because the neurons in the same feature map (or output image) 120 have identical weights or parameters. These local shared weights reduce the complexity of the network such that when multi-dimensional input data enters the network, the CNN reduces the complexity of data reconstruction in the feature extraction and regression or classification process.

In mathematics, a tensor is a geometric object that maps in a multi-linear manner geometric vectors, scalars, and other tensors to a resulting tensor. Convolutions operate over 3D tensors (e.g., vectors), called feature maps (e.g., 120), with two spatial axes (height and width) as well as a depth axis (also called the channels axis). In general computer vision, a CNN is typically designed to classify color images that contain three image channels—Red, Green and Blue (RGB). For an RGB image, the dimension of the depth axis is three (3), because the image has three color channels, Red, Green, and Blue. For a black-and-white picture, the depth is one (1) (i.e., levels of gray). The convolution operation extracts patches 122 from its input feature map and applies the same transformation to all of these patches, producing an output feature map 124. This output feature map is still a 3D tensor, having a width and a height. Its depth can be arbitrary, because the output depth is a parameter of the layer, and the different channels in that depth axis no longer stand for specific colors as in RGB input; rather, they stand for filters. Filters encode specific aspects of the input data at a height level. A single filter could be encoded with, for example, morphology, texture, or size of a follicle.

Convolutions are defined by two key parameters:

(1) size of the patches extracted from the inputs—typically 1×1, 3×3 or 5×5 and (2) depth of the output feature map—the number of filters computed by the convolution. In general, these start with a depth of 32, continue to a depth of 64, and terminate with a depth of 128 or 256.

A convolution operates by sliding these windows of size 3×3 or 5×5 over a 2D or 3D input feature map, stopping at every location, and extracting a patch 122 of surrounding features [shape (window Height, window Width, input Depth)]. Each such patch is then transformed (via a tensor product with the same learned weight matrix, called the convolution kernel) into an ID vector of shape (output_depth). All of these vectors are then spatially reassembled into, for example, a 3D output map of shape (Height, Width, output Depth). Every spatial location in the output feature map corresponds to the same location in the input feature map (for example, the lower-right corner of the output contains information about the lower-right corner of the input).

During training, a CNN is adjusted or trained so that the input data leads to a specific output estimate. The CNN is adjusted using back propagation based on a comparison of the output estimate and the ground truth (i.e., true label) until the output estimate progressively matches or approaches the ground truth. The CNN is trained by adjusting the weights (w) or parameters between the neurons based on the difference between the ground truth and the actual output. The weights between neurons are free parameters that capture the model's representation of the data and are learned from input/output samples. The goal of model training is to find parameters (w) that minimize an objective loss function L(w), which measures the fit between the predictions of the model parameterized by w and the actual observations or the true label of a sample. The most common objective loss functions are the cross-entropy for classification and mean-squared error for regression. In other implementations, the convolutional neural network uses different loss functions such as Euclidean loss and softmax loss.

Currently CNNs are trained with stochastic gradient descent (SGD) using mini-batches. SDG is an iterative method for optimizing a differentiable objective function (e.g., loss function), a stochastic approximation of gradient descent optimization. Many variants of SGD are used to accelerate learning. Some popular heuristics, such as AdaGrad, AdaDelta, and RMSprop tune a learning rate adaptively for each feature. AdaGrad, arguably the most popular, adapts the learning rate by caching the sum of squared gradients with respect to each parameter at each time step. The step size for each feature is multiplied by the inverse of the square root of this cached value. AdaGrad leads to fast convergence on convex error surfaces, but because the cached sum is monotonically increasing, the method has a monotonically decreasing learning rate, which may be undesirable on highly nonconvex loss surfaces. Momentum methods are another common SGD variant used to train neural networks. These methods add to each update a decaying sum of the previous updates. In other implementations, the gradient is calculated using only selected data pairs fed to a Nesterov's accelerated gradient and an adaptive gradient to inject computation efficiency. The major shortcoming of training using gradient descent, as well as its variants, is the need for large amounts of labeled data. One way to deal with this difficulty is to resort to the use of unsupervised learning. Data augmentation is essential to teach the network the desired invariance and robustness properties, when only few training samples are available.

The convolution layers (e.g., 106,110) of a CNN serve as feature extractors. Convolution layers act as adaptive feature extractors capable of learning and decomposing the input data into hierarchical features. In one implementation, the convolution layers take two images as input and produce a third image as output. In such an implementation, convolution operates on two images in two-dimension (2D), with one image being the input image 104 and the other image, the kernel (e.g., 102), applied as a filter on the input image 104, producing an output image. The convolution operation includes sliding the kernel 102 over the input image 104. For each position of the kernel 102, the overlapping values of the kernel and the input image 104 are multiplied and the results are added. The sum of products is the value of the output image 120 at the point in the input image 104 where the kernel 102 is centered. The resulting different outputs from many kernels are called feature maps (e.g., 120,124).

Once the convolutional layers (e.g., 106, 110) are trained, they are applied to perform recognition tasks on new inference data. Since the convolutional layers learn from the training data, they avoid explicit feature extraction and learn implicitly from the training data. Convolution layers use convolution filter kernel weights, which are determined and updated as part of the training process. The convolution layers extract different features of the input image 104, which are combined at higher layers (e.g., 108,110,112). A CNN uses a various number of convolution layers, each with different convolving parameters such as kernel size, strides, padding, number of feature maps, and weights.

Sub-sampling layers (e.g., 108, 112) reduce the resolution of the features extracted by the convolution layers to make the extracted features or feature maps (e.g., 120,124) robust against noise and distortion, reduce the computational complexity, to introduce invariance properties, and to reduce the chances of overfitting. It summarizes the statistics of a feature over a region in an image. In one implementation, sub-sampling layers (e.g., 108,112) employ two types of pooling operations: average pooling and max pooling. The pooling operations divide the input into non-overlapping two-dimensional spaces. For average pooling, the average of the four values in the region is calculated for pooling. The output of the pooling neuron is the average value of the input values that reside with the input neuron set. For max pooling, the maximum value of the four values is selected for pooling. Max pooling identifies the most predictive feature within a sampled region and reduces the resolution and memory requirements of the image.

In a CNN, a non-linear layer is implemented for neuron activation in conjunction with convolution. Non-linear layers use different non-linear trigger functions to signal distinct identification of likely features on each hidden layer (e.g., 106,110). Non-linear layers use a variety of specific functions to implement the non-linear triggering, including the Rectified Linear Unit (ReLU), PreLU, hyperbolic tangent, absolute of hyperbolic tangent, and sigmoid and continuous trigger (non-linear) functions. In a preferred implementation, ReLUs are used for activation. The advantage of using the ReLU function is that the convolutional neural network is trained many times faster. ReLU is a non-continuous, non-saturating activation function that is linear with respect to the input if the input values are larger than zero and zero otherwise. In other implementations, the non-linear layer uses a power unit activation function.

A CNN can also implement a residual connection which comprises reinjecting previous representations into the downstream flow of data by adding a past output tensor to a later output tensor, which helps prevent information loss along the data-processing flow. Residual connections address two common problems that plague any large-scale deep-learning model: vanishing gradients and representational bottlenecks. A residual connection makes the output of an earlier layer available as input to a later layer, effectively creating a shortcut in a sequential network. Rather than being concatenated to the later activation, the earlier output is often summed with the later activation, which assumes that both activations are the same size. If they are of different sizes, a linear transformation can be used to reshape the earlier activation into the target shape.

Residual learning of a CNN was originally proposed to solve the performance degradation problem, where the training accuracy begins to degrade along with the increasing of network depth. By assuming that the residual mapping is much easier to be learned than the original unreferenced mapping, a residual network explicitly learns a residual mapping for a few stacked layers. A residual network stacks a number of residual units to alleviate the degradation of training accuracy. Residual blocks make use of special additive skip connections to address vanishing gradients in deep neural networks. At the beginning of a residual block, the data flow is separated into two streams. The first carries the unchanged input of the block, while the second applies weights and non-linearities. At the end of the block, the two streams are merged using an element-wise sum (or subtraction). The main advantage of such constructs is to allow the gradient to flow through the network more easily. Residual networks enable CNNs to be easily trained and improved accuracy for applications such as image classification and object detection.

A known problem in deep learning is the covariate shift where the distribution of network activations changes across layers due to the change in network parameters during training. The changing scale and distribution of inputs at each layer implies that the network has to significantly adapt its parameters at each layer and thereby training has to be slow (i.e., use of small learning rate) for the loss to keep decreasing during training (i.e., to avoid divergence during training). A common covariate shift problem is the difference in the distribution of the training and test set which can lead to suboptimal generalization performance.

In one implementation, Batch Normalization (BN) is proposed to alleviate the internal covariate shift by incorporating a normalization step, a scale step, or a shift step. BN is a method for accelerating deep network training by making data standardization an integral part of a network architecture. BN guarantees more regular distributions at all inputs. BN can adaptively normalize data even as a mean variance change over time during training. It internally maintains an exponential moving average of the batch-wise mean and variance data. The main effect is to aid with gradient propagation similar to residual connections. The BN layer can be used after a convolutional, densely, or fully connected layer but before the outputs are fed into an activation function. For convolutional layers, the different elements of the same feature map—i.e. the activations at different locations—are normalized in the same way in order to obey the convolutional property. Thus, all activations in a mini-batch are normalized over all locations, rather than per activation.

The one or more convolutional layers 106,110, interspersed with one or more sub-sampling layers 108, 112 are typically followed by one or more fully connected (FC) layers 114,116. FC layers are used to concatenate the multi-dimension feature maps (e.g., 120,124, etc.) and to make the feature map into a fixed-size category and generating a feature vector for a classification output layer 118. FC layers are typically the most parameter and connection intensive layers. In one implementation, global average pooling is used to reduce the number of parameters and optionally replace one or more FC layers for classification, by taking the spatial average of features in the last layer for scoring. This reduces the training load and bypasses the overfitting issues. The main idea of global average pooling is to generate the average value from each last layer feature map as the confidence factor for scoring, feeding directly into a softmax layer, which maps for example, 3D inputs into [0,1].

This allows for interpreting one or more output layers 118 as probabilities and selection of pixels (2D inputs) or voxels (3D inputs) with the highest probability.

In one implementation one or more autoencoders are used for dimensionality reduction. Autoencoders are neural networks that are trained to reconstruct the input data, and dimensionality reduction is achieved using a fewer number of neurons in the hidden layers (e.g., 106,110, etc.) than in the input layer 104. A deep autoencoder is obtained by stacking multiple layers of encoders with each layer trained independently (pretraining) using an unsupervised learning criterion. A classification layer can be added to the pretrained encoder and further trained with labeled data (fine-tuning).

Figure 2:
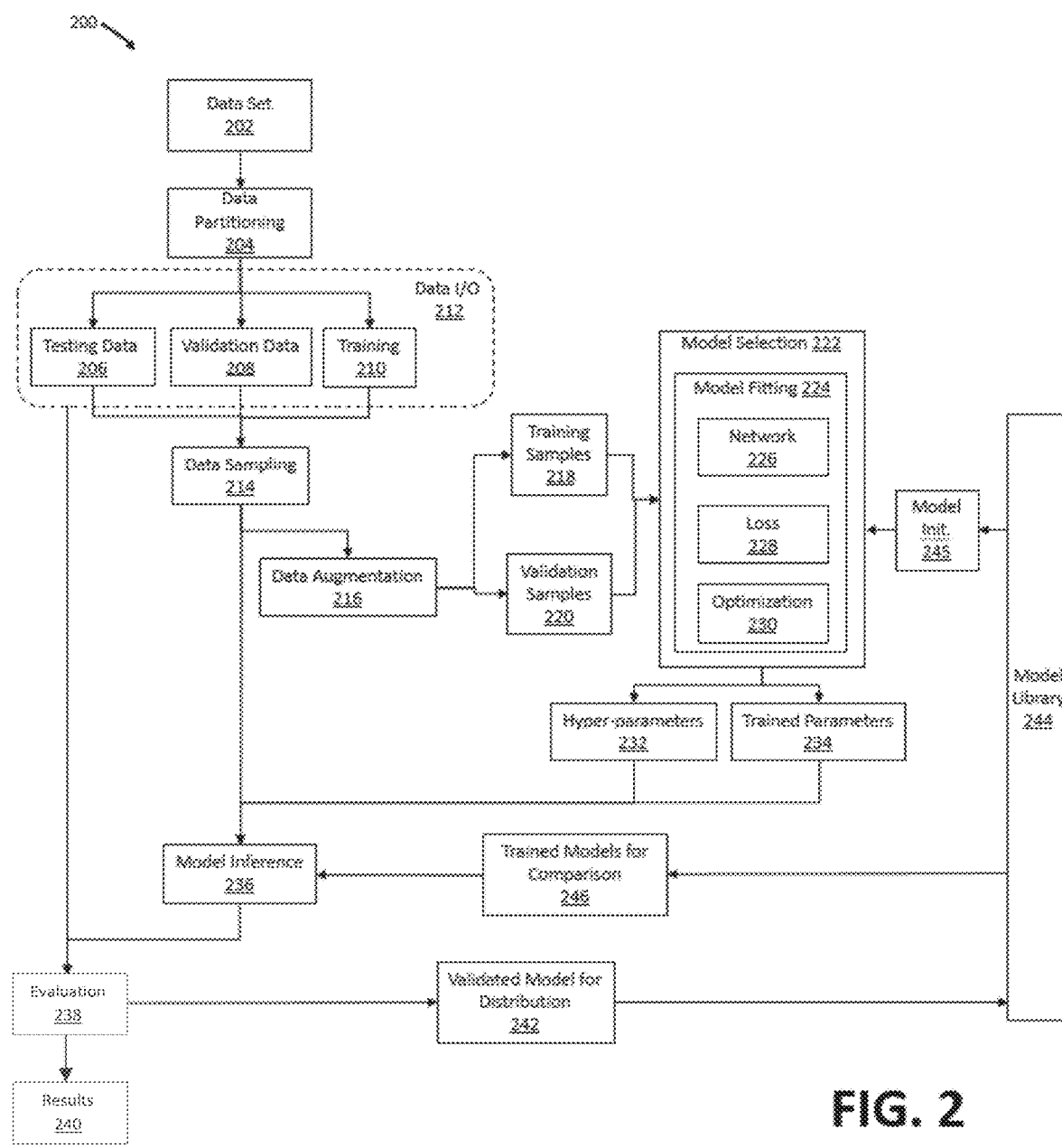
FIG. 2 is a schematic of a deep learning (DL) pipeline development process, in accordance with an embodiment of the present disclosure.

FIG. 2 is a schematic 200 of a deep learning (DL) pipeline development process, according to various embodiments. A DL pipeline development comprises three phases: model selection (model selection and fitting on a training data set), model evaluation, and model distribution. In a preferred embodiment, an infrastructure is created to train, evaluate and distribute one or more ANN networks. In various embodiments one or more data set are correctly isolated to avoid biased evaluations, through a data set flow 202 and data partitioning step 204 into testing data set 206, validation data 208, and training data 210. In various embodiments, the one or more said dataset is processed through a data 10 step 212 and then sampled 214, in different various ways depending on the phase of the pipeline. In applications with limited data, data sets are augmented 216 to compensate for small training data sets, wherein the training data set is too sparse to represent the variability in the distribution of images. Data augmentation artificially increases the variability of the training data set by introducing random perturbations during training, for example applying random spatial transformations or adding random image noise. In various embodiments, training and validation data samples are introduced (steps 218, 220) into a model selection 222. In various embodiments, the model selection process comprises a model fitting process 224 that includes configuring a network 226, selection of a loss function 228, and an optimization 230 process. In various embodiments, the output of the model selection 222 process comprises one or more hyper-parameter 232 and trained parameter 234. In various embodiments, the data of said parameters flow into a model inference 236 process whereby data from sampling 214 are included systematically to process the whole data set 202. The model is evaluated 238 to generate one or more result 240. In various embodiments, one or more validation model can be stored 242 in a model library 244 where stored models can be used to initialize step 245 model during model selection 222 or for trained model comparison 246 during model inference 236. In DL, it is common practice to adapt previous network architectures, trained or untrained, in part or in full for similar or different tasks. In various embodiments, model library 244 enables storing of models and parameters that are dependent on the application domain being addressed; for example, denoising, object detection, counting, and prediction. One or more network architecture can be constructed using a library (e.g., TensorFlow), which provides the tools for defining computational pipelines and executing them efficiently on hardware resources. One or more software application drivers may be used to define a common structure for one or more components of the pipeline.

Ultrasound images are affected by a strong multiplicative noise, the speckle, which generally impairs the performance of automated operations, like classification and segmentation, aimed at extracting valuable information for the end user. An object of the present disclosure is a DL approach, implemented preferably through one or more CNN. In various implementations, given a suitable set of images, a CNN is trained to learn an implicit model of the data, for example, noise to enable the effective de-speckling of new data of the same type. Noise in US images can vary in shape, size, and pattern, being nonlinear. The premise is that image speckle noise can be expressed more accurately through non-linear models. In various embodiments, the CNN architecture is assembled for learning a non-linear end-to-end mapping between noisy and clean US images with a dilated residual network (US-DRN). In various implementations, one or more skip connections together with residual learning are added to the denoising model to reduce the vanishing gradient problem. In various preferred embodiments, the model directly acquires and updates the network parameters from the training data and the corresponding labels in lieu of relying on a priori knowledge of a pre-determined image or a noise description model. Without being bound to theory, contextual information of an image can facilitate the recovery of degraded regions. In general, deep convolution networks can mainly enhance the contextual information through enlarging the receptive field by increasing the network depth or enlarging the filter (e.g. 102 of FIG. 1). However, as the network depth increases, the accuracy becomes "saturated" and then degrades rapidly. Enlarging the filter size can lead to more convolution parameters that greatly increase the computing power and training time. In various implementations, dilated convolutions are employed to both enlarge the receptive field while maintaining filter size. A common convolution receptive field has a linear correlation with the layer depth. In contrast, a dilated convolution receptive field has an exponential correlation with the layer depth. As an example, for a kernel size=3×3, the dilation factors of the 3×3 dilated convolutions of an architecture with 7 layers, are set 1, 2, 3, 4, 3, 2, 1, respectively. In one implementation, a lightweight model comprises 7 dilated convolutions.

Figure 3:
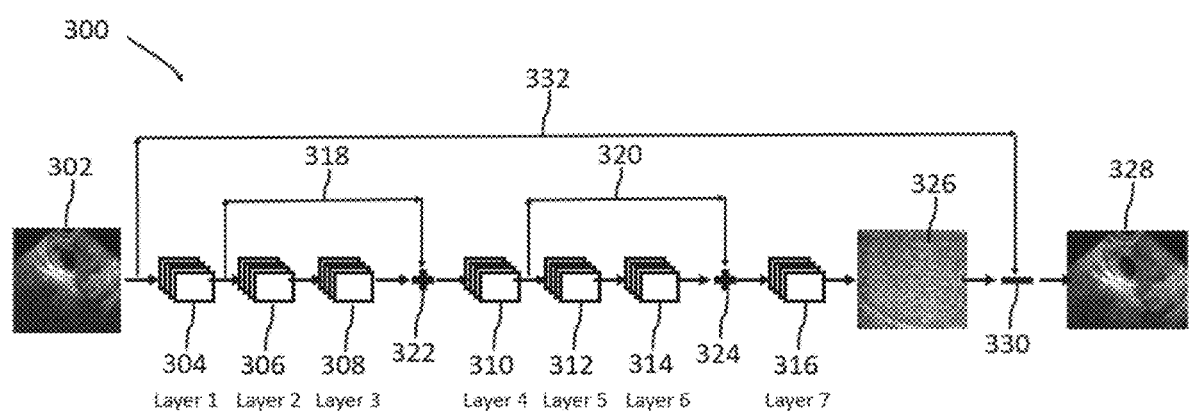
FIG. 3 is a schematic of the US-DRN architecture, in accordance with an embodiment of the present disclosure.

Referring to FIG. 3 a schematic 300 of the US-DRN architecture is shown, according to various embodiments. In various implementations, the architecture comprises one or more image 302 that serve as an input to one or more convolution layer 304, 306, 308, 310, 312, 314, 316, each operating similarly to layer 106 of FIG. 1. In various embodiments, the architecture is a residual network comprising one or more skip connections 318, 320, element-wise sum 322, 324, passing one or more feature information from a previous layer to a posterior layer while maintaining the image details and avoiding or reducing the vanishing gradient problem. In various embodiments, the network learns a resulting estimated components of speckle image (or subtracting image) 326. An output denoised image 328 is produced by subtracting image 326 from input image 302 with element-wise subtractor 330 via skip connection 332. In various alternative embodiments, element-wise subtractor 330 can comprise a division-wise element. In this implementation, the input image 302 is divided by estimated speckle image 326. The result is then passed through a non-linear function layer, optionally a hyperbolic tangent layer, to produce a denoised image 328. Training becomes much more effective by setting a dual goal of reproducing the noise. This is important for the detection, recognition, segmentation, or classification of a reproductive anatomy for ART given the inherent scarcity of training data. The implementation of residual mapping can lead to more effective learning and rapidly reducing the loss function after passing through a multi-layer network. Without being bound to theory, most pixel values in a residual image are close to zero and the spatial distribution of the residual feature maps should be very sparse, leading the gradient descent process to a smoother hyper-surface of loss to filter parameters. The search for an allocation that is close to optimal becomes quicker and easier, enabling the addition of more layers to the network to improve performance.

Figure 4:
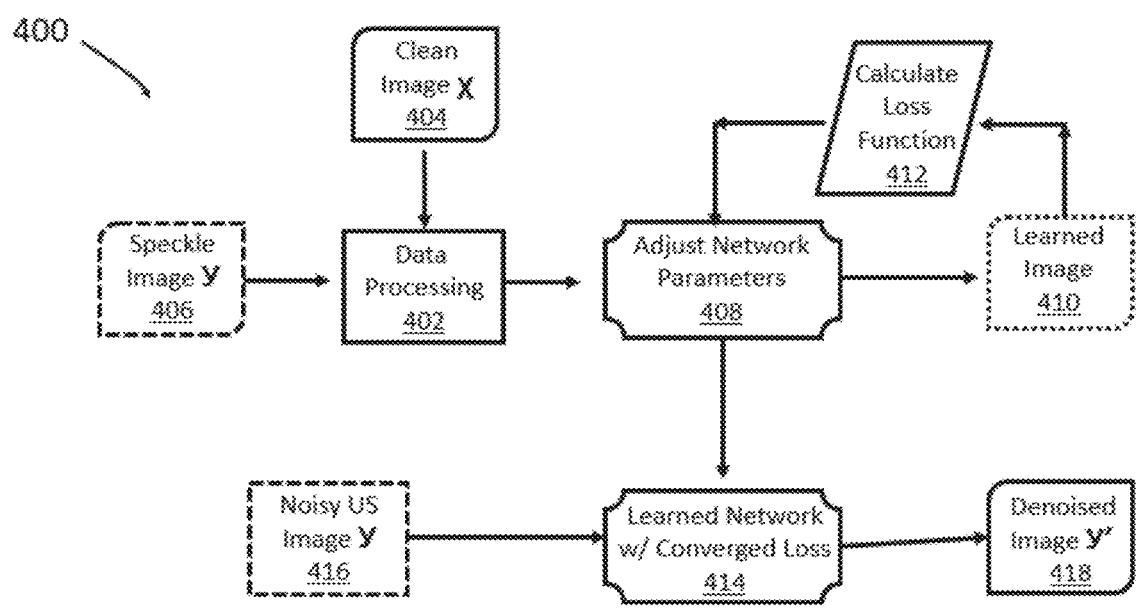
FIG. 4 is a flowchart of a deep learning network for the US image de-speckling process, in accordance with an embodiment of the present disclosure.

FIG. 4 is a flowchart 400 of a deep learning network for the US image de-speckling process, according to various embodiments. The three main procedures involved in this method are data processing of a training dataset, CNN training, and image de-speckling. In various embodiments, data processing (step 402) comprises the processing of a clean image 404 and a speckled image 406 that can include normalization and division of an image into smaller patches. The divided patches provide inputs into a feedforward network for CNN training. One or more noisy patches (e.g., kernel 102 of FIG. 1) from speckled image 406 provide inputs and the clean patches of clean image 404 are target outputs. In one implementation, back-propagation SDG can reduce the error and increase accuracy. In various embodiments, a patch undergoes a feedforward process and then back-propagation to update one or more network parameter step 408. A patch is randomly selected for input and used only once in the training process as SGD is adopted for optimization. The network selects one input patch with a corresponding clean patch, calculates the error between the clean patch and network output, and then calculates the errors between different hidden layers (e.g., 204,206,208 of FIG. 2). In each iteration a new learned image 410 is created that is subsequently improved via further minimization of the loss function by calculation 412. The weights are updated in network parameter step 408 by adding the current values with the calculation results of the partial derivative of error. After updating, the error and loss between a patch x and patch y decrease is to be used to de-speckle new images from a learned network 414 with parameters obtained by minimal loss convergence. The results of the trained network are a collection of weights and thresholds. The learned network 414 enables a noisy image 416 to be de-speckled into a denoised image (or clean image) 418.

In various non-limiting embodiments, the training of said US-DRN comprises the use of 100 to 500 images, optionally obtained from a US scanner or device, that are further resized, (e.g., 256×256). In various embodiments, one or more 2D channel can be assigned to a corresponding axial, coronal or sagittal slices in a Volume of Interest (VOI). In various embodiments, a 3D US dataset is resampled to extract one or more VOI at differing physical scales with a fixed number of voxels. Each VOI can be translated along a random vector in 3D space for N number of repetitions. Each VOI may also be translated around a randomly oriented vector for N number of repetitions by one or more random angles for expansion of the training dataset. In various embodiments, the size of a kernel or patch can be selectively set (e.g., 40×40) as well as the stride (e.g., 1 to 10). In various embodiments, network training comprises the use of an optimization method (e.g., ADAM optimization) as the gradient descent method, mini-batches (e.g., 16) with a learning rate (e.g., 0.0002), over several epochs (e.g. 20, etc.). In various embodiments, the training regularization parameter is set equal to a chosen value (e.g., 0.002). In various embodiments, the denoiser model training platform comprises the optional use of Matlab R2014b (Mathworks company in Natick, Mass., USA), the CNN toolbox was MatConvnet (MatConvnet-1.0-beta24, Mathworks, Natick, Mass.), and the GPU platform Nvidia Titan X Quadro K6000 (NVIDIA Corporation, Santa Clara, Calif.). In various embodiments, alternative CNN toolbox comprises a proprietary framework, or one or more open framework, including but not limited to, Caffe, Torch, GoogleNet, as well as alternative deep learning models including, but not limited to, VGG, LeNet, AlexNet, ResNet, U Net, the like, or combinations thereof. In various embodiments, the performance evaluation of the filter system and method comprises the use of, but not limited to, standard deviation (STD), peak signal-to-noise ratio (PNSR), equivalent looks (ENL), and edge preservation index (EPI), the structural similarity index measurement (SSIM), and an unassisted measure of the quality of the first-order and second-order descriptors of the denoised image ratio (UM). The higher the PSNR value is, the stronger the denoising ability of the algorithm. If the ENL value is bigger, the visual effect is better. The EPI value reflects the retentive ability of the boundary, and a bigger value is better. The SSIM indicates the similarity of the image structure after denoising, and it is as big as possible. The UM does not depend on the source image to assess the denoised image—when the value is smaller, the ability of the speckle suppression is stronger. In various embodiments, the method comprises the use of 3D convolution to extract more information compared to using multiple input channels to perform 2D convolution.

Figure 5:
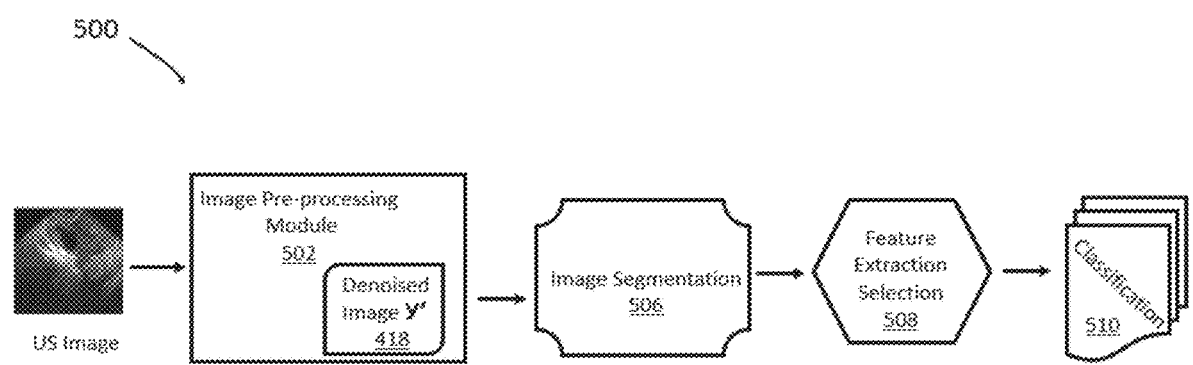
FIG. 5 is a schematic of a computer-aided diagnosis (CAD) architecture and processing method, in accordance with an embodiment of the present disclosure.

An object of the present disclosure is an ANN system and method for object detection, recognition, annotation, segmentation, or classification of at least one US image, preferably using a denoised image processed by the said US-DRN architecture, in the provision of ART for the diagnosis, treatment and clinical management of clinical infertility. FIG. 5 is a schematic 500 of a computer-aided diagnosis (CAD) architecture and processing method, according to various embodiments. In various embodiments, the CAD architecture comprises one or more modular components including an image pre-processing module 502, an image segmentation module 506, and feature Extraction and Selection module 508, and a Classification module 510. In various embodiments, image preprocessing module 502 executes one or more steps, including but not limited to, enhancement, smoothing or reduction of speckle, resulting for example, in a denoised image 418 of FIG. 4. In various embodiments, image segmentation module 506 executes one or more steps, including but not limited to, partitioning of the image into one or more non-overlapping regions, and one or more identified regions of interest (ROIs) or VOIs are separated from the background. In various embodiments, one or more ROI or VOI is used for feature extraction. In various embodiments, feature Extraction and Selection module 508 executes one more step, including but not limited to, feature extraction or removal, selection of a subset of features to build and optimal set of features for accurate distinguishing of one or more relevant features of a reproductive anatomy. In various embodiments, a Classification module 510 executes one more step, including but not limited to, applying classification techniques to classify one or more reproductive anatomy. In various embodiments, a chosen CNN architecture and method enable the detection, recognition, annotation, segmentation, or classification of a(n): ovary, cyst, cystic ovary, polycystic ovary, follicle, antral follicle, or the like.

An object of the present disclosure is a framework for object detection, recognition, annotation, segmentation, or classification of at least one US image, using one or more software Application drivers in the provision of ART for the diagnosis, treatment and clinical management of clinical infertility. In various embodiments one or more application driver defines a common structure for a particular module function of CAD system described in FIG. 5. The Application functions to instantiate data, application objects, and distribution of workload as well as combining results from various computational resources (e.g., multiple CPU or GPUs). The Application driver delegates application-specific functionality to separate Application classes. In various embodiments, an Application driver can be configured from a command line or programmatically using a human-readable configuration file, preferably containing the data set definitions and settings that can deviate from defaults. The Application classes encapsulate standard analysis by connecting, including but not limited to, a Reader driver to load data, a Sampler driver to generate data samples for processing, a Network driver, preferably a CNN, to process the inputs (e.g., 418 of FIG. 4), and an Output handler (comprising drivers, for example, Loss function 228 driver and Optimization 230 driver of FIG. 2) and an Aggregator driver during inference and evaluation. In various embodiments, a driver further comprises one or more sub-components, for example, to perform data augmentation.

CAD systems for analysis encompass a number of tasks or applications of a clinical work flow: detection, registration, reconstruction, enhancement, model representation, segmentation, classification, etc. Different applications use different types of inputs and outputs, different networks, and different evaluation metrics. In a preferred embodiment, the framework platform is designed in a modular fashion to support the addition of any new Application type, by encapsulation of workflows in Application classes. The Application class defines the required data interface for the Network and Loss function, facilitates the instantiation of data sampler and output objects, connects them as required, and specifies the training regimen. In a non-limiting example, during training, a uniform Sampler driver enables the generation of small image patches and corresponding labels, processed by said CNN to generate segmentations, using a Loss function driver to compute the loss used for backpropagation using an Adam Optimizer function driver. During inference, a Grid Sampler driver can generate a set of non-overlapping patches to convert the image to segment, the said network to generate corresponding segmentations, and a Grid Sample Aggregator driver to aggregate the patches into a final segmentation.

A DL architecture comprises a complex composition of simple functions that can be simplified in by repeated reuse of conceptual blocks. In one implementation, the framework platform comprises conceptual blocks represented by encapsulated Layer classes, or inline using, for example, the TensorFlow's scoping system. In various embodiments, one or more composite layers are constructed as simple compositional layers and TensorFlow operations. In one implementation, visualization of the network graph is automatically supported as a hierarchy at different levels of detail using the TensorBoard visualizer. In various embodiments, Layer objects define one or more scope upon instantiation, enabling repeated reuse to allow complex weight-sharing without breaking encapsulation. In various embodiments, one or more Reader classes enable the loading of image file from one or more medical file format for a specific data set and applying image-wide pre-processing. In various implementations, the framework platform uses nibabel to facilitate a wide range of data format. In a preferred embodiment, the framework platform incorporates flexibility in mapping from input dataset into packets of data to be processed and from the processed data into useful outputs. The former is encapsulated in one or more Sampler classes, and the latter is encapsulated in Output handlers. The instantiation of matching Samplers and Output handlers is delegated to the Application class. Samplers generate a sequence of packets of corresponding data for processing. Each packet contains all the data for one independent computation (e.g., one step of gradient descent during training), including images, labels, classifications, noise samples or other data needed for processing. During training, samples are taken randomly from the training data, while during inference and evaluation the samples are taken systematically to process the whole data set. During training, the Output handlers take the network output, compute a loss and the gradient of the loss with respect to the trainable variables, and use an Optimizer driver to iteratively train the model. During inference, the Output handlers generate useful outputs by aggregating one or more network outputs and performing any necessary post-processing (e.g. resizing the outputs to the original image size). In various embodiments, Data augmentation and Normalization within the platform are implemented as Layer classes applied in the Sampler. In a preferred embodiment, the framework platform enables supports for mean, variance and histogram intensity data normalization, and flip, rotation and scaling for spatial Data augmentation.

Figure 6:
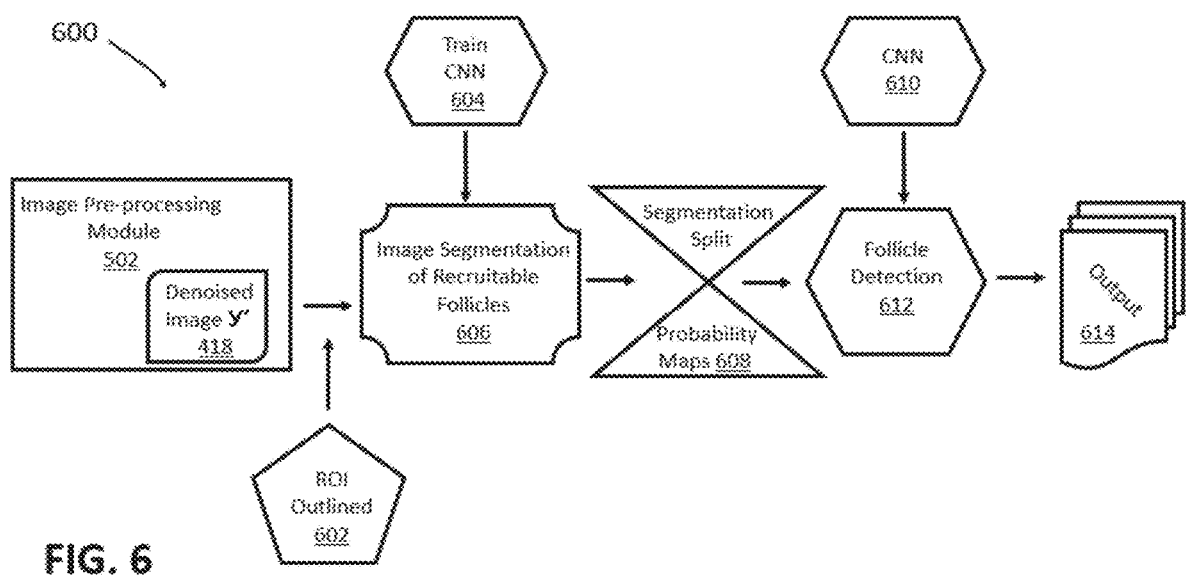
FIG. 6 is a schematic flow chart of a process for the detection of a "recruitable" follicle, in accordance with an embodiment of the present disclosure.

FIG. 6 is a schematic flow chart 600 of a process for the detection of a "recruitable" follicle. The detection process comprises a cascade CNN base method. Firstly, one or more ROI or VOI of at least one US image, denoised and preprocessed using, for example, image processing module 502 of FIG. 5, is coarsely delineated or outlined (step 602) by a skilled ultrasonographer or physician as to serve as a training data set. Secondly, a CNN (e.g., n-convolution and n-pooling layers) is trained 604 to segment "recruitable" follicles 606 and generates corresponding segmentation probability maps 608. Thirdly, all the segmentation probability maps are split into different connected regions, using one or more operators, including but not limited to, binarization operator, erosion operator, or a dilation operator. Finally, a CNN 610 is employed to detect a "recruitable" follicle 612, generating an output 614, based on US images patches re-labeled by one or more split segmentation probability maps 608.

Figure 7:
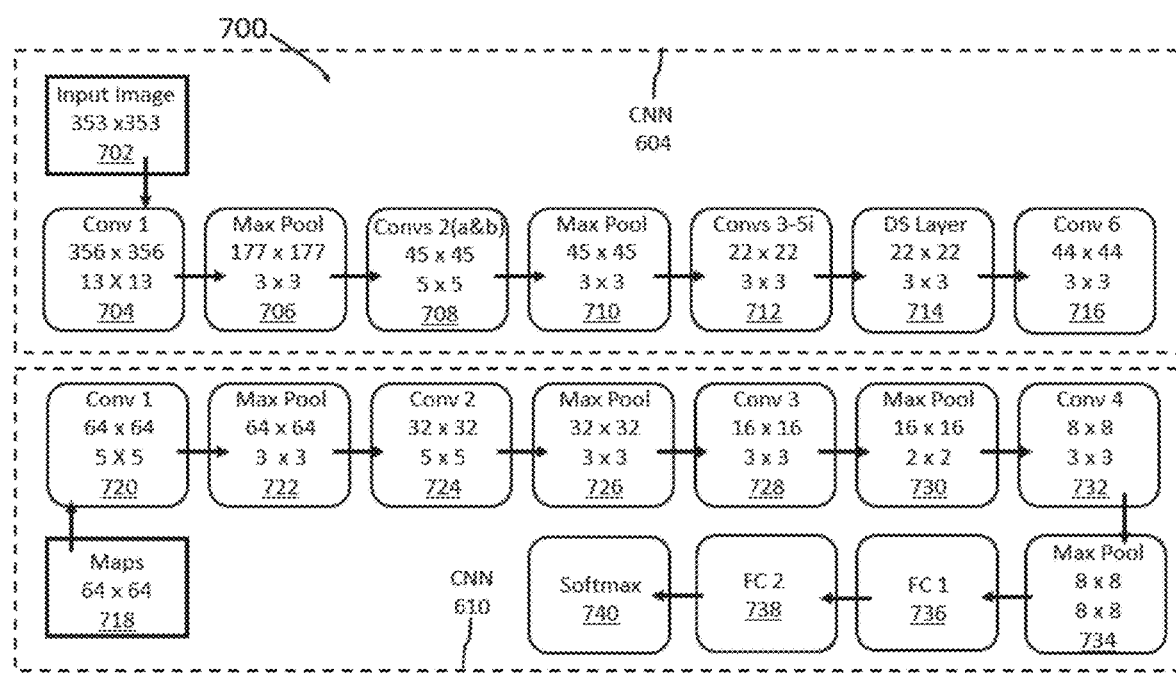
FIG. 7 is a schematic of the CNN architectures for detection of "recruitable" follicles, in accordance with an embodiment of the present disclosure.

Referring to FIG. 7, a schematic of the CNN architectures for detection of "recruitable" follicles is shown, according to an embodiment. In this non-limiting implementation, an image (e.g., 418 of FIG. 4) is introduced as input into a first convolution layer (Cony) 704 of CNN 604 architecture of FIG. 6 that generates one or more feature maps 706 using one or more filter (e.g., 13×13), a stride size of 2 pixel and a padding size of 6×6 pixels, subsequently subject max pooling. The following convolution layers 708 both generate 265 feature maps 710 of size 45×45 through filters of size 5×5. A padding size of 2 pixels and a stride size of 2 pixels are used in the second convolution layer. Max pooling reduces the sizes of the feature maps further. A padding size of 2 pixels and stride size of 1 pixel are used in subsequent layers 712. The residual convolution layers comprise of padding size of 1 pixel and a stride size of 1 pixel. Moreover, each of the residual convolutional layers 712, 714 except the last two convolutional layers, comprises filters of size 3×3, generates 384 feature maps of size 22×22. The second to last one convolutional layer 714, with filters of size 3×3, generates 256 feature maps of size 22×22. The last convolutional layer 716, with filters of size 3×3, generates one feature map of size 44×44. Two max-pooling layers 706, 710 with window size of 3×3 follow after the first convolutional layer 704 and the third convolutional layers 708, respectively. In one embodiment, a stride size of two pixels are used in these two pooling layers. A padding size of one pixel is only, optionally, used in the first pooling layer 706. In addition, the function parametric rectified linear unit (PReLu) is used as the activation function, whose parameters can be adaptively learned using one or more said learning methods of the present disclosure. Further, for follicle detection, the CNN 610 architecture comprises four convolutional layers 720, 724, 728, 732, four pooling layers 722, 726, 730, 734, and two fully-connected layers 736, 738 with 64, 1 output, respectively. The first convolutional layer 720 generates from maps 718 (e.g., 608 of FIG. 6) feature maps of size 64×64 through filters of size 5×5, with a stride size of one pixel, and a padding size of two pixels. The second convolutional layer 724 generates 64 feature maps of size 32×32 through filters of size 5×5, with a padding size of two pixels and a stride size of one pixel. The third convolutional layer 728 generates 64 feature maps of size 16×16 through filters of size 3×3, with a padding size of one pixel and a stride size of one pixel. The last convolutional layer 732 generates 384 feature maps of size 8×8 through filters of size 3×3, with a padding size of one pixel and a stride size of one pixel. In a preferred embodiment, the feature maps in current layers are connected to all of the feature maps in the previous layers. The first two convolutional layers 720,724 are both followed by the max-pooling layers 722, 726 with a padding of 1, a stride of 2, and window size of 3. The third convolutional layer 728 is followed by the max-pooling layer 730 with a stride of 2, and window size of 2. The fourth convolutional layer 732 is followed by the max-pooling layer 734 with a stride of 8, and window size of 8. The activation function is rectified linear unit (ReLU), which is the point-wise nonlinearity applied to all hidden units. In various embodiments, a local response normalization scheme is also applied after each of the ReLU operations. After the output of the second fully-connected layer 738, a softmax layer 740 is used to generate a distribution over the class labels (e.g., non recruitable or recruitable follicle) by minimizing the cross-entropy loss between the predicted labels (i.e. recruitable follicle) and ground truth labels (i.e., a priori segmented recruitable follicle).

In one implementation, the training process for detecting recruitable follicle comprises three steps. Firstly, CNN 604 of FIG. 6 is trained with random initialized parameters using data containing patches extracted from the images of recruitable follicles. In one implementation, the image patches of size (e.g., 353×353 702 of FIG. 7) cropped sampled randomly from these recruitable follicle images are inputs of the CNN 604 of FIG. 6. They are labeled by probability maps with pixel values in the interval [e.g., 0:1; 0:9], which are determined according to the relation between the image patches and their corresponding binary masks. The segmentation probability maps 608 of FIG. 6 about recruitable follicles are the outputs of the CNN 604 of FIG. 6. In various embodiments, improved performance comprises the use of a multi-view strategy to train the CNN 604 of FIG. 6. Secondly, one or more splitting method, consisting of continuous binarization operator, erosion operator and dilation operator, is to split connected regions of the segmentation probability maps generated by the CNN 604 of FIG. 6 into several isolated connected regions. For example, the continuous binarization operator, with the values from a step 0.01 interval [0:15; 0:7], can be used to binarize the segmentation probability maps 608 of FIG. 6. In various embodiments, one or more workflow applications of said framework platform described in FIG. 5 can be implemented to perform the one or more module function of the process for identification, detection segmentation, or classification of one or more recruitable follicle. In various embodiments, the model training platform comprises the optional use of Matlab R2014b (Mathworks company in Natick, Mass., USA), the CNN toolbox was MatConvnet (MatConvnet-1.0-beta24, Mathworks, Natick, Mass.), and the GPU platform Nvidia Titan X Quadro K6000 (NVIDIA Corporation, Santa Clara, Calif.). In various embodiments, alternative CNN toolbox comprises a proprietary framework, or one or more open framework, including but not limited to, Caffe, Torch, GoogleNet, as well as alternative deep learning models including, but not limited to, VGG, LeNet, AlexNet, ResNet, U Net, the like, or combinations thereof. In various embodiments, the detection process enables detection, identification, segmentation, or classification of alternative reproductive anatomy (ies) and not limited to "recruitable" follicles, including but not limited to, a (n): ovary, cyst, cystic ovary, polycystic ovary, follicle, antral follicle, or the like. In various embodiments, one or more results are electronically recorded in at least one electronic health record database. In alternative embodiments, the said results are transmitted and stored within a database residing in a cloud-based server.

An object of the present disclosure is the said ANN system and method for an object detection framework in the provision of ART for the diagnosis, treatment and clinical management of clinical infertility. In various embodiments, the said system and method enables object detection (e.g., follicle detection), localization, counting, and tracking (e.g., follicle growth rate) over time of one or more reproductive anatomy from one or more US images. In various embodiments, one or more detectors or classifiers are trained in the pixel space, where the locations of one or more target reproductive anatomy(ies) are labeled (e.g., follicle). For follicle detection, the output space comprises one or more sparsely labeled pixel indicating follicle centers. In various embodiments, the output space is encoded to a compressed vector of fixed dimension, preferably shorter than the original sparse pixel space (i.e., compressed sensing). In various embodiments, a CNN regresses the said vector from the input pixels (e.g., US image). In various embodiments, follicle locations on the output pixel is recovered using normalization, including but not limited to, $L_1$ normalization.

Without being bound to theory, the Nyquist-Shannon sampling theorem states that a certain minimal sampling rate is require for the reconstruction of a band-limited signal. Compressed sensing (CS) has the potential to reduce the sampling and computation requirements for sparse signals under a linear transformation. The premise of CS is that an unknown signal of interest is observed (sensed) through a limited number of linear observations. It has been proven that it is possible to obtain a stable reconstruction of the unknown signal from these observations, under the assumptions that the signal is sparse and matrix dis-coherence. The signal recovery technique generally relies on convex optimization methods with a penalty expressed by L1 normalization, for example orthogonal match pursuit or augmented Lagrangian method.

Figure 8:
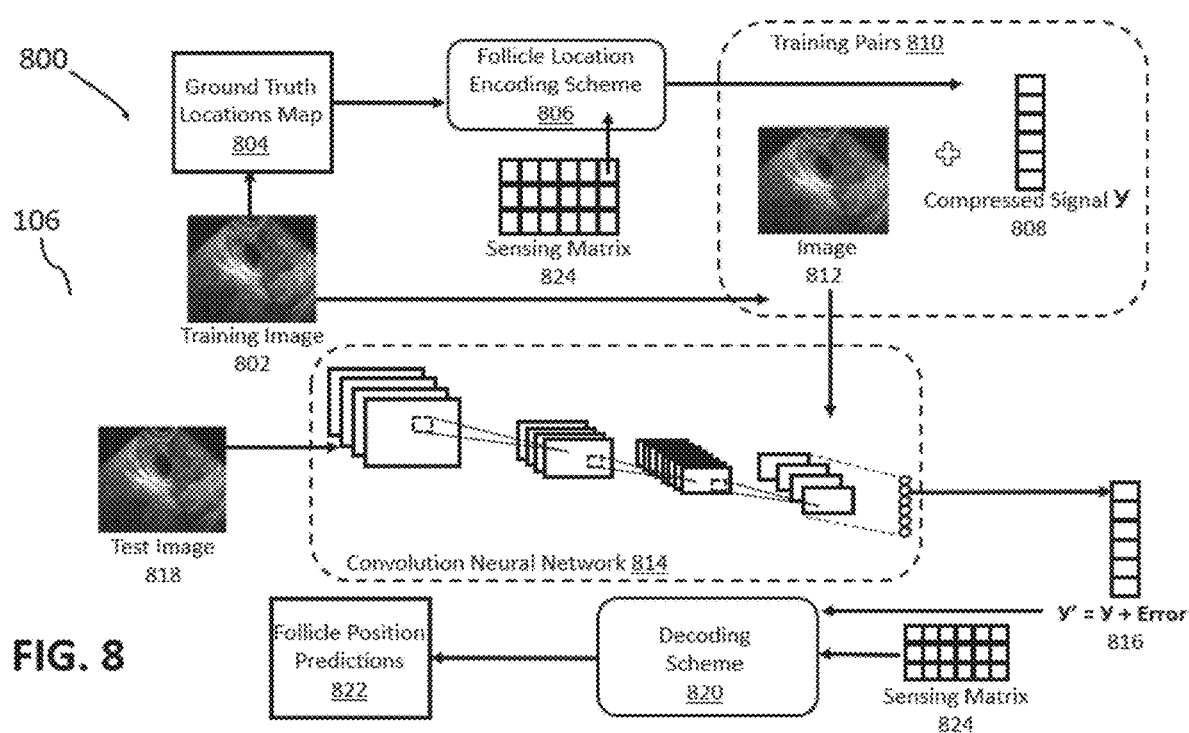
FIG. 8 is a flow chart of the follicle detection and localization framework, in accordance with an embodiment of the present disclosure.

Referring to FIG. 8, a flow chart 800 of the follicle detection and localization framework is shown, according to various embodiments. The framework comprises a follicle localization encoding phase using one or more random projection, a CNN based regression model to capture one or more relationship between a US image and the encoded signal y, and a decoding phase for recovery and detection. In various embodiments, during training, the ground truth locations of follicles are indicated by a pixel-wise binary annotation map 804. In various embodiments, one or more encoding scheme 806 converts a follicle location from the pixel space representation of image 802 to a compressed signal y 808. Then training pairs 810, each consisting of a US image 812 (e.g., 418 of FIG. 4) containing one or more follicles and compressed signal y 808, to train a CNN 814 to function as a multi-label regression model. In one implementation, a Euclidean loss is employed during training, given suitability for a performing regression. In various embodiments, data augmentation comprises one or more image rotation of the training sets for robustness to rotations. In various embodiments, during testing, the trained CNN 814 generates an output for an estimated signal y' 816 for each test image 818 provided as input to the first convolution layer. Subsequently, a decoding scheme 820 is used to estimate the ground truth follicle location prediction 822 by performing $L_1$ minimization recovery on the estimated signal y' 816, with one more sensing matrix 824, determined by one or more encoding or decoding schemes.

A number of encoding and schemes may be employed by the said framework. In various embodiments, the framework employs one or more random projection-based encoding schemes. In various embodiments, the center of every follicle is attached with a dot mark, a cross mark, or a bounding box. In one embodiment, pixel-wise binary annotation map 804 comprises a size of w-by-h indicating the location of one or more follicles by labeling 1 at the pixel of the follicle centroids, otherwise label 0 at background pixels. In one embodiment, annotation map 804 is vectorized by the concatenation of every row of map 804 into a binary vector f length wh. Therefore, a positive element in map 804 with {x,y} coordinates will be encoded to the [x+h(y−1)]-th position in the vector f. A random projection is applied after the generation of vector f. Vector f can be represented by one or more linear observation y, which is proportional to sensing a matrix 824 and vector f. Without being bound to theory, sensing matrix 824 preferably satisfies one or more conditions, including but not limited to, isometric property. In one implementation, matrix 824 is a random Gaussian matrix. In alternative embodiments, another encoding scheme 806 is employed, particular for processing of large images, to reduce computational burden. In various embodiments, the coordinates of every follicle centroid are projected onto multiple observation axes. A set of observation axes are created with an N total number of observations. In one implementation, the observation axes are uniformly distributed around image 802. For the n-observation axis $oa_n$, the location of follicles is encoded into a R-length sparse signal. Perpendicular signed distances ($f_n$) are calculated from follicles to the n-observation axis $oa_n$. Thus, $f_n$ contains signed distances as a measure of distance and location of which side of $oa_n$ follicles. The encoding of follicle locations under $oa_n$ is $y_n$, obtained by a random projection. Similarly, $y_n$ is a proportional matrix 824 times $f_n$, the signed distances. In various embodiments, the process is repeated for all the N observation axes to obtain each $y_n$. The joint representation of follicle locations is derived from the encoding result y after concatenation of the total $y_n$. Similarly, a decoding scheme is be employed by the said framework to recover the vector f. In various embodiments, accuracy recovery from the encoded signal y is obtained by solving an $L_1$ normalization convex optimization problem. The recovery off enables the localization of every true follicle, localized N time, with N predicted positions 822.

The follicle detection and localization framework comprise one or more CNN 814 for building at least one regression model between a US image 812 and its follicle location representation or compressed signal y 808. In one implementation, CNN 814 comprises a network consisting of, but not limited to, 5 convolution layers and 3 fully connected layers. In an alternative implementation, CNN 814 comprises a deep neural network, for example with a 100-layer model. In other implementations, CNN 814 comprises one or more CNN disclosed within the present disclosure. In various embodiments, one or more loss function may be employed, including but not limited to, Euclidean loss, or other said loss functions of the present disclosure. In various embodiments, the dimension of the output layer of said CNN may be modified to the length of compressed signal y 808. In various embodiments, one or more CNN 814 model may be further optimized using additional learning methods, including but not limited to Multi-Task Learning (MTL), for localization and follicle counting. In various embodiments, during training, one or more labels are provided to an CNN. In one implementation, an encoded vector y carrying pixel-level location information of follicles. In another implementation, a scalar or follicle count (c), representing the total number of follicles in training image patch, filter, or kernel. In various embodiments, two or more said labels may be concatenated into a final training label. One or more loss function is then applied on the combined label. Therefore, the supervision information for both follicle detection and counting can be jointly used for optimizing the CNN model parameters. A large number of square patches may be employed for training. Along with each training patch, a signal (i.e. the encoding result: y) may be employed to indicate the location of target follicles present in each patch. Data augmentation may be employed by performing patch rotation on the collection of training patches making the system rotation invariant. In various embodiments, one or more MTL framework may be employed to address the cases of touching and clustered follicles. In one implementation, one or more follicle appearance, including but not limited to, texture, morphology, borders, contour information are integrated into an MTL framework to form a deep-contour aware network, preferably the complementary appearance and contour information can further improve the discriminative capability of intermediate features, and hence more accurately separate the touching or clustered follicle into individual ones. In various embodiments, the CNNs are trained in an end-to-end manner to boost performance. In various embodiments, the model training platform comprises the optional use of Matlab R2014b (Mathworks company in Natick, Mass., USA), the CNN toolbox was MatConvnet (MatConvnet-1.0-beta24, Mathworks, Natick, Mass.), and the GPU platform Nvidia Titan X Quadro K6000 (NVIDIA Corporation, Santa Clara, Calif.). In various embodiments, alternative CNN toolbox comprises a proprietary framework, or one or more open framework, including but not limited to, Caffe, Torch, GoogleNet, as well as alternative deep learning models including, but not limited to, VGG, LeNet, AlexNet, ResNet, U Net, the like, or combinations thereof. In various embodiments, the said process enables detection, localization, and counting of alternative reproductive anatomy (ies) and not limited to follicles, including but not limited to, a (n): ovary, cyst, cystic ovary, polycystic ovary, or the like. In various embodiments, one or more results are electronically recorded in at least one electronic health record database. In alternative embodiments, the said results are transmitted and stored within a database residing in a cloud-based server.

Figure 9:
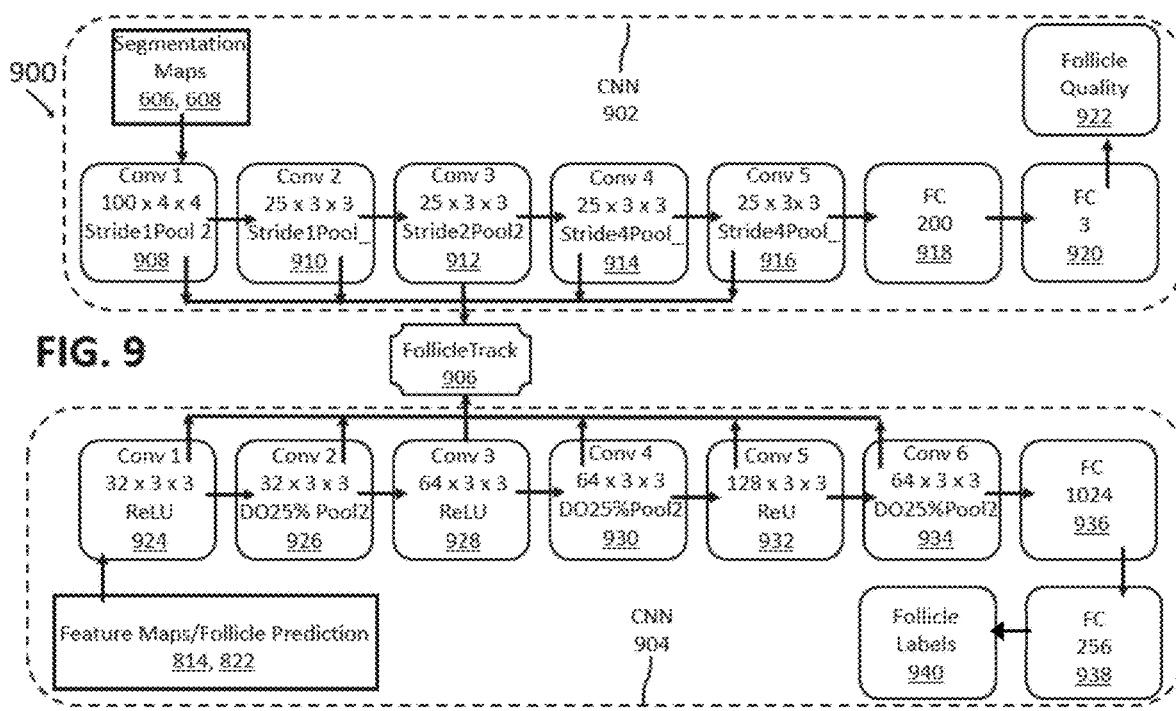
FIG. 9 is a flow chart of the follicle tracking framework, in accordance with an embodiment of the present disclosure.

Referring to FIG. 9, a flow chart 900 of the follicle tracking framework is shown, according to various embodiments. The follicle tracking framework comprises one or more CNN 902, 904 specifically tasked for distinguishing follicle size, volume, or quality and then using the network to generate tracking feature maps in real-time. In various embodiments, the tracking framework learns a correlation filter specifically for each tracked follicle, training on features extracted by the CNN 902, 904. In various implementations, deep semantics are combined with spatial resolution of early filters for combined accurate tracking. In a preferred embodiment, at least one said network is trained to perform multiple tasks, taking advantage of pre-computing feature maps from one or more CNN network segmentation processes, for example, 606,608 of FIG. 6. The follicle tracking system comprises a hierarchical tracker to perform correlation-filter tracking based on extracted features. In various embodiments, the tracker computes one or more circularized kernels in Fourier space to increase performance. At each tracked follicle, a search window is located over the follicle in the first frame of the input. This frame is the set of neural network features obtained from one or more segmentation map output (e.g., 606, 608 of FIG. 6). Once a search window is positioned, one or more correlation filters are learned by minimizing a loss function, optionally performed in the Fourier space domain. At each tracking time step, the correlation filters are matched features within a search window Z overlaid on the last known location of the target follicle, obtained from one or more feature map 814 or follicle position prediction 822 of FIG. 8. In various embodiments, at least one filter is trained on one or more layers of a selected CNN. In various embodiments, at each time step, one or more correlation filters are matched features within a search window Z overlaid on the last known location of a target follicle. One or more matches are computed, preferably in the Fourier space domain. In various embodiments, one or more deep filters are propagated to higher layer levels in a weighted manner. One or more estimated new location is discovered by taking an argmax $f_o$ of $\{m,n\}$ and a new search is realigned to the new location. Referring again to FIG. 9, in various embodiments, FollicleTrack 906 takes as input one or more segmented images (e.g., 814, 822 of FIG. 8) indicating one or more location of a tracking target follicle, preferably the first frame of a time-series sequence, one or more raw images, one or more processed images, or feature maps output (e.g., 606,608 of FIG. 6), one or more convolution layers of CNN 902 and CNN 904. One or more follicles can be selected for tracking, or segmented follicles can be tracked across the time series. In various embodiments, the time-series (e.g., sec, min, hr, day, etc.) sequence comprises one or more sequence of, including but not limited to, real-time transvaginal US images, stored sequences of transvaginal US images, retrieved images from a US scanner/device, transmitted from a US scanner/device. In various embodiments, CNN 902 is a deep convolutional neural network designed to further segment follicles in terms of physical dimensions and changes in dimensions. One or more training sets are used to train the network enabling the segmentation of follicle by size, shape, volume, distribution, average, standard deviation, morphology, position, displacement, growth rate from US images (e.g., 2D, 3D, etc.). In various implementations, one or more output of Follicle-Track 906 is a list containing, including but not limited to, one or more learned filter for each follicle, history of follicle centroid position (s) at each timestep, history of follicle location, follicle distribution (size, volume, etc.), movement, displacement, growth rate (size, volume, etc.). In various embodiments, the output data enables the annotation of one or more segmented or unlabeled images, or to directly map follicle trajectories (e.g., movement, growth rate). In various embodiments, US images are obtained from a historical database containing curated information on recruitable follicles, non-recruitable follicles, differentiated by size or volume, the like or combinations thereof. In various embodiments, the US images are annotated by a skilled ultrasonographer or a physician with expertise in the recognition of reproductive anatomy, preferably differentiating features of an optimal follicle, size, follicle distribution, volume, growth rate, for extraction and implantation. In various embodiments, CNN 902 comprises, but is not limited to, five convolution layers 908, 910, 912, 914, 916, followed by a fully connected layer 918, feeding into a final FC 920. One or more output 922 includes but is not limited to follicle size/volume range, distribution, average, standard deviation, or growth rate (e.g., 1 mm per day) of one or more follicle. In various embodiments, CNN 902 produces one or more set of masks and feature maps, per at least one frame of US image input, obtained from at least one patient, from at least one visit for follicle tracking. In various embodiments, CNN 904 is a deep convolutional neural network designed to further segment follicles in terms of quality or changes in quality. In one implementation, CNN 904 comprises six 3×3 convolution layers 924, 926, 928, 930, 932, 934, with ReLu activation, maxpool layer 936 and a softmax layer 938 layer, and output 940. In various implementations, drop out is implemented at one or more levels of the network. In one implementation, the network is programmed to produce output feature maps from each convolution layer as well as label classification scores. In various embodiments, the said convolution layers produce one or more feature maps for inter-follicle discrimination. In various embodiments, the said hierarchical method is combined with one or more other networks of the present disclosure to improve tracking accuracy. In one implementation, a weighted correlation filter at each search window provides a cost to a linear assignment, augmenting its ability to track follicles. In various embodiments, the model training platform comprises the optional use of Matlab R2014b (Mathworks company in Natick, Mass., USA), the CNN toolbox Mat-Convnet (MatConvnet-1.0-beta24, Mathworks, Natick, Mass.), and the GPU platform Nvidia Titan X Quadro K6000 (NVIDIA Corporation, Santa Clara, Calif.). In various embodiments, alternative CNN toolbox comprises a proprietary framework, or one or more open framework, including but not limited to, Caffe, Torch, GoogleNet, as well as alternative deep learning models including, but not limited to, VGG, LeNet, AlexNet, ResNet, U Net, the like, or combinations thereof. In various embodiments, the said process enables detection, localization, counting, and tracking of alternative reproductive anatomy (ies) and not limited to follicles, including but not limited to, a (n): oocyte, blastocyte, ovary, cyst, cystic ovary, polycystic ovary, endometrial thickness, or the like. In various embodiments, one or more results are electronically recorded in at least one electronic health record database. In alternative embodiments, the said results are transmitted and stored within a database residing in a cloud-based server.

Figure 10:
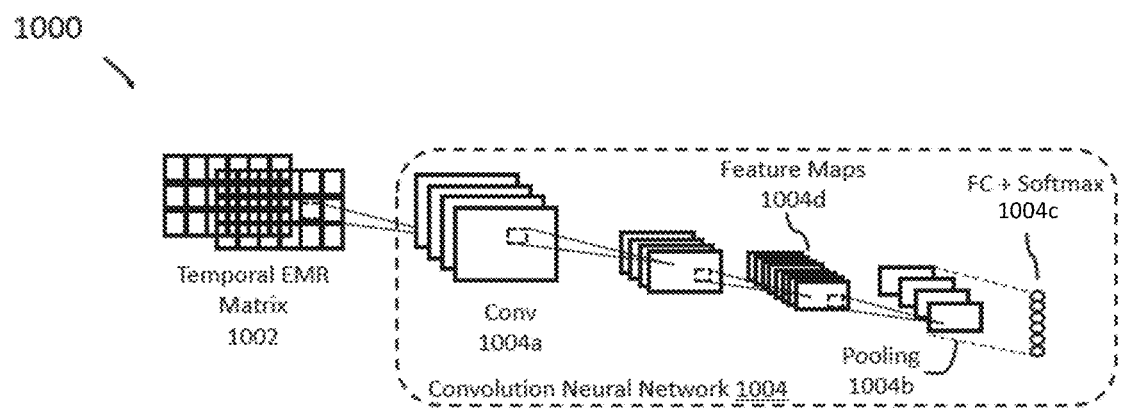
FIG. 10 is a diagram of an EMR data convolution network architecture, in accordance with an embodiment of the present disclosure.

An object of the present disclosure is the said ANN system and method for analyzing an electronic medical record in the provision of ART for the diagnosis, treatment and clinical management of clinical infertility. In various embodiments, said system and method enable feature extraction or phenotyping of one or more patients from at least one longitudinal patient electronic medical record (EMR), electronic health record (EHR), database, or the like. Electronic phenotyping refers to the problem of extracting effective phenotypes from longitudinal patient health records. The challenges of effective extraction of features from a patient's EMR or EHR are high-dimensionality due to the large quantity of distinct medical events, temporality in which EHRs evolve over time, and sparsity of data, irregularity, and systematic errors or bias. A temporal matrix representation of data is employed to address representation of patient medical records as temporal matrices with one dimension corresponding to time and the other dimension corresponding to medical events. In various embodiments, temporal EHR information or medical record is converted into one or more binary sparse matrix, comprising horizontal dimension (time) and a vertical dimension (medical event). In one implementation, the (i,j)-entry in the matrix of a specific patient is equal to 1 if the i-th event is recorded or observed at time stamp j in the patient medical record. Referring to FIG. 10, a diagram 1000 of an EMR data convolution network architecture is shown, according to various embodiments. The architecture comprises a first layer (or matrix) 1002 containing one or more patient EMR matrix and CNN 1004. In various embodiments, CNN 1004 further comprises one or more convolution layer 1004a, preferably a one-side convolution layer, a pooling layer 1004b, preferably for introducing sparsity on the learning features, and an FC layer 1004c. In various embodiments, cony layer 1004a comprises a convolution operator on the time dimension of the patient EMR matrix 1002. In one implementation, each event matrix 1002 of length 1 is represented by vector X, with x as a d-dimension event vector corresponding to the i-th event items. In various embodiments, $x_{i:\ i+j}$ represents the concatenation of items $x_i$, $x_{i+1}$, . . . $x_{i+j}$. A one-sided convolution filter operation comprises a filter applied to window of n event features to produce a new feature. For example, a feature c is generated from a window of events (e.g., $x_{i:\ i+n-1}$) using one or more non-linear activation function, preferably ReLU. The filter is applied to each possible window of features in one or more event matrix 1002 to produce a feature map 1004d. Mean pooling layer 1004b is applied over one or more feature map 1004d to obtain an average value of c. In a preferred embodiment, one or more important feature with the highest value for each feature map is captured for feature extraction. The FC layer 1004c is a fully connected layer linking with one or more softmax classifiers for classification or prediction using one or more single-frame.

EMR data vary widely in time and temporal connectivity is required for prediction. In various embodiments, temporal smoothness is incorporated into the learning process using one or more temporal fusion. In various embodiments, one or more data sample is processed as a collection of short, fixed-sized sub-frames, of a single frame, containing several contiguous intervals in time. In one implementation, a model fuses information across the temporal domain, performed early in the network 1004, by modifying convolution layer 1004a to extend in time. In one implementation, proximal fusion combines information across an entire time window immediately on the basic event feature level. One or more filters of the convolution layer 1004a are modified to extend operation on one or more sub-frames. In another implementation, a distal fusion model performs fusion on the fully connected layer 1004c. In one embodiment, one or more separate single-frame network or sub-frames are merged in the fully connected layer, whereby detecting patterns existing in one or more sub-frames. In another implementation, a balance between proximal and distal temporal fusion enables the slow fusing of information throughout the network. In various embodiments, the higher layers of network receive progressively more global information in time. In one implementation, connectivity is extended to all convolution layers in time and the fully connected layer 1004c can compute global pattern characteristics by comparison of all output layers. The framework enables the production of insightful patient phenotypes by taking advantage of the higher order temporal event relationships. In various embodiments, one or more recording of neuron activity enables the observation of patterns indicative of a health or medical condition. In one implementation, one or more neurons outputs receive the highest weights, preferably normalized, in one or more top layer for positive or negative classification of a condition. One or more regions appearing a training set highly activating one or more corresponding neurons can be identified using one or more sliding window cut (min,max window size) to obtain one or more top ranked regions or patterns. In another implementation, one or more weights of neurons are aggregated and assigned to a medical or health condition, and important features for patient phenotype extraction and predictive purposes. In various embodiments, the model training platform comprises the optional use of Matlab R2014b (Mathworks company in Natick, Mass., USA), the CNN toolbox MatConvnet (Mat-Convnet-1.0-beta24, Mathworks, Natick, Mass.), and the GPU platform Nvidia Titan X Quadro K6000 (NVIDIA Corporation, Santa Clara, Calif.). In various embodiments, alternative CNN toolbox comprises a proprietary framework, or one or more open framework, including but not limited to, Caffe, Torch, GoogleNet, as well as alternative deep learning models including, but are not limited to, VGG, LeNet, AlexNet, ResNet, U Net, the like, or combinations thereof.

In various embodiments, the said medical record comprises one or more stored patient record, preferably records of patients undergoing infertility treatment, ultrasound image, images of said reproductive anatomy, physician notes, clinical notes, physician annotation, diagnostic results, body-fluid biomarkers, hormone markers, hormone level, neohormones, endocabinoids, genomic biomarkers, proteomic biomarkers, Anti-Mullerian hormone, progesterone, FSH, inhibins, renin, relaxin, VEGF, creatine kinase, hCG, fetoprotein, pregnancy-specific b-1-glycoprotein, pregnancy-associated plasma protein-A, placental protein-14, follistatin, IL-8, IL-6, vitellogenin, calbindin-D9k, therapeutic treatment, treatment schedule, implantation schedule, implantation rate, follicle size, follicle number, AFC, follicle growth rate, pregnancy rate, date and time of implantation (i.e., event), CPT code, HCPCS code, ICD code, or the like. In various embodiments, the one or more patient phenotypes include, but are not limited to, infertility, anovulation, oligo ovulation, endometriosis, male factor infertility, tubal factor infertility, decreased ovarian reserve, patient risk of ovulation, patient having the optimal characteristics for implantation, patient ready for implantation, patient having one or biomarkers indicative of ovulation, patient having US images indicative of being optimal for extraction, etc. In various embodiments, one or more identified patient phenotype or predictive result from an output layer of said one or more CNN are recorded in at least one electronic health record database. In alternative embodiments, the said results are transmitted and stored within a database residing in a cloud-based server.

Figure 11:
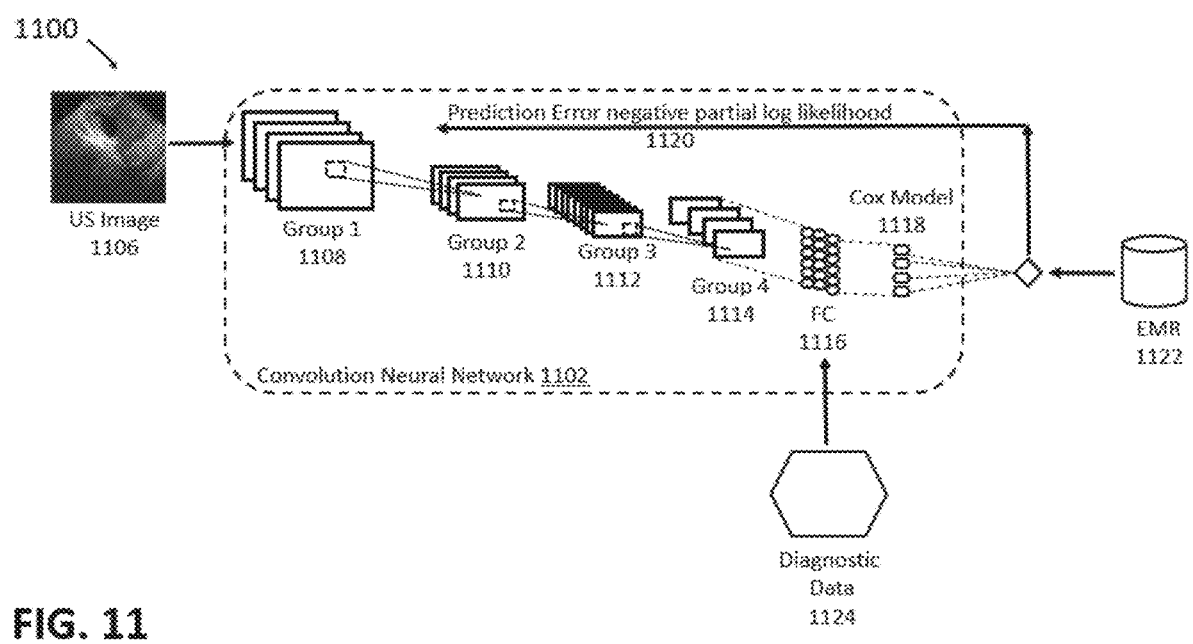
FIG. 11 is a schematic diagram of a survival convolution neural network architecture, in accordance with an embodiment of the present disclosure.

An object of the present disclosure is the said ANN system and method for predictive planning in the provision of ART for the diagnosis, treatment and clinical management of clinical infertility. A unified predictive framework comprises one or more survival convolution neural networks ("SCNNs") to provide one or more prediction of time-to-event outcomes from at least one US image and one or more patient phenotype obtained from a patient medical record. In various embodiments, the framework comprises one or more image sampling and risk filtering technique for predictive purposes. In one implementation, one or more ROIs or VOIs of at least one US image is used to train a deep CNN seamless integrated with a Cox proportional hazards model to predict patient outcomes, including but not limited to, induction-termination of hormone therapy, having recruitable follicle, having dominant follicle, having matured follicle, ready for follicle extraction, optimal endometrial thickness for implantation. Referring to FIG. 11, a schematic diagram 1100 of a survival convolution neural network architecture is shown, according to various embodiments. The architecture comprises an n-layer CNN architecture 1102 with a Cox proportional hazards model 1118 to predict time-to-event data from an image 1106. In one non-limiting implementation, image feature extraction is achieved by four groups of convolutional layers. The first group 1108 comprises two convolutional layers with 64 3×3 kernels interleaved with local normalization layers and then followed with a single maximum pooling layer. The second group 1110 comprises two convolutional layers (128 3×3 kernels) interleaved with two local normalization layers followed by a single maximum pooling layer. The third group 1112 interleaves four convolutional layers (256 3×3 kernels) with four local normalization layers followed by a single maximum pooling layer. The fourth group 1114 contains interleaves of eight convolutional (512 3×3 kernels) and eight local normalization layers, with an intermediate pooling layer and a terminal maximum pooling layer. These four groups are followed by a sequence of three fully connected layers 1116 containing 1,000, 1,000, and 256 nodes, respectively. The terminally fully connected layer outputs a risk (e.g., likelihood of being extracted for implantation) prediction associated with the input image 1106. The predicted risks are input into a Cox proportional hazards model 1118 to calculate a negative partial log likelihood 1120, to provide an error signal for backpropagation within CNN 1102. In various embodiments, one or more optimization methods are employed to optimize model weights, biases, and convolution kernels, for example, Adagrad algorithm. In one implementation, the nonlimiting parameters of Adagra include an initial accumulator value (e.g., 0.1), initial learning rate (e.g., 0.001), and an exponential decay factor (e.g., 0.1). In one implementation, model weights are initialized using, for example, a variance scaling method, and a weighing decay (e.g., 4e-4) applied to the fully connected layers during training. In various embodiments, mini-batches (containing e.g., recruitable follicle) are used for training, preferably over multiple epochs (e.g., 100; 1 epoch is one complete cycle through all training samples). In various embodiments, each mini-batch produces a model update, resulting in multiple updates per epoch. In one implementation, Cox likelihood is calculated locally within each mini-batch to perform updates. In another implementation, randomization of one or more mini-batch assignments are used at the beginning of each epoch to improve robustness. In yet another implementation, regulation is applied during training, optionally using random dropout 5% of weights in the last fully connected layer of fully connected layers 1116 in each mini-batch during training to avoid over fitting. During training, one or more identified "recruitable" follicle field (e.g., pixel area or volume sufficient to differentiate recruitable/non-recruitable) are sampled from a region (e.g., ROI or VOI) and treated as semi-independent training samples. In various embodiments, each recruitable follicle identity/field is paired with a patient time-to-event outcome from a medical record database 1122. In various embodiments, patient outcome information includes, but is not limited to, days on hormone therapy, demographic, age, presence or absence of one or more said diagnostic biomarker, therapeutic treatment, chronic biomarker, clinical notes, physician observations, follicular growth rate, follicle size, history of pregnancy, initiation-termination ovarian stimulation, number of cycle day, follicle retrieval, follicle recruitment, oocyte retrieval, follicle stage, follicle maturity, egg maturity, fertilization rate, blastocyst embryo development, embryo fragmentation, embryo growth rate, embryo grade, embryo trophectoderm grade, embryo inner cell mass grade, embryo size, embryo growth rate, embryo cell count, embryo metabolic parameters, embryo metabolome, embryo maturity, blastocyst development rate, embryo euploidy, embryo aneuploidy, embryo mosaicism, embryology database, embryo quality, implantation, or the like In various embodiments, duplicate outcomes can be paired with one or more regions containing multiple follicles. One or more regions can be sampled at the beginning of each training epoch to generate a new set of ROIs or VOIs. In various implementations, randomization via transformation (e.g., translation, rotation, contrast, brightness, etc.) can be applied to an acquired field to improve robustness to follicle orientation or image variations. In various embodiments, one or more fields are sampled from each ROI or VOI for calculating a risk prediction using said SCNN 1102. For example, when predicting the outcome of a patient, 10 fields are sampled from each ROI to generate a representative collection of fields, and a risk is predicted for each field. In one implementation, a median field risk is calculated in each region, sorted and filtered, and the second highest value is selected as the patient risk. The selection of the second highest risk introduces robustness to outliers or high risks that occur due to image quality or artifacts. In various embodiments, the filter procedure enables the selection of fields using a conservative prognosis to ensure the accurate selection of recruitable follicles for implantation. In various embodiments, one or more diagnostic data 1124 may be incorporated into the SCNN 1102 to improve prognostic accuracy. In one implementation, the SCNN 1102 learns from diagnostic biomarkers and US images simultaneously by incorporating biomarker variables to influence the patterns learned by the network via patient blood work information during a visit. In one embodiment, the diagnostic data 1124 is incorporated into the fully connected layers 1116. In various embodiments, one or more prediction models are trained optionally using TensorFlow (v0.12.0) on servers equipped with dual Intel(R) Xeon(R) CPU E5-2630L v2 @ 2.40 GHz CPUs, 128 GB RAM, and dual NVIDIA K80 graphics cards. In various embodiments, alternative CNN toolbox comprises a proprietary framework, or one or more open framework, including but not limited to, Caffe, Torch, GoogleNet, as well as alternative deep learning models including, but not limited to, VGG, LeNet, AlexNet, ResNet, U Net, the like, or combinations thereof. In various embodiments, one or more patient time-to-event outcome predictive result from an output layer of said one or more CNN are recorded in at least one electronic health record database. In alternative embodiments, the said results are transmitted and stored within a database residing in a cloud-based server.

An object of the present disclosure is a computer program product for use in the provision of ART for the diagnosis, treatment and clinical management of clinical infertility.

Figure 12:
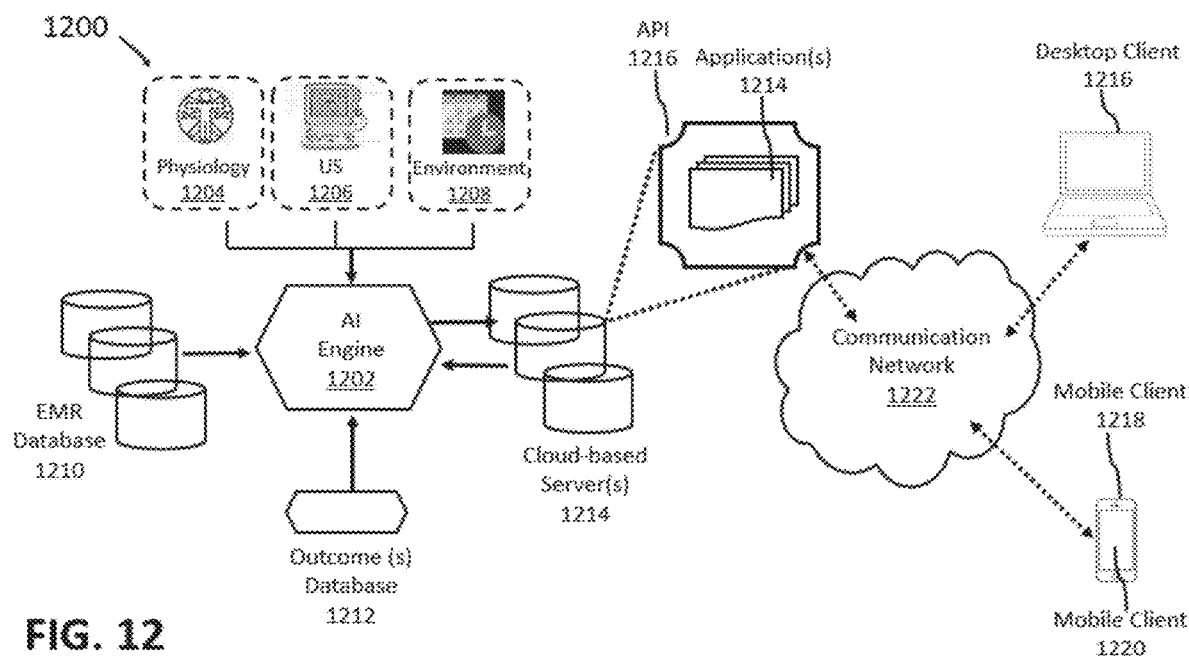
FIG. 12 is a schematic of a computer product architecture, in accordance with an embodiment of the present disclosure.

Referring to FIG. 12, a schematic 1200 of a computer product architecture is disclosed, according to various embodiments. The architecture comprises an AI Engine 1202 that receives one or more inputs from one or more sources of data. In one embodiment, AI Engine 1202 receives data from a plethora of sources, preferably, but not limited to, physiology data 1204, US imaging data 1206, and environmental data 1208. In various embodiments, physiology data 1204 comprises one or more said diagnostic results, data, biomarkers, genomic marker, proteomic marker, body fluid analyte, chem panel, measured hormone levels, or the like. In various embodiments, US image data 1206 comprises one or more said US image, retrieved from a US scanner/device, US image stored external to an US scanner/device, US image processed by one or more said CNN of the present disclosure. In various embodiments, environmental data 1208 comprises one or more said longitudinal collected medical record data, number of cycle day, time of day, week, or monthly data. The AI Engine 1202 can also receive inputs from one or more EMR database 1210 and one or more outcomes database (or cloud-based server) 1212. In various embodiments, EMR database 1210 comprises one or more longitudinal patient medical records, said records of patient under infertility treatment or management. In a similar manner, outcomes database 1212 comprises one or more longitudinal infertility patient medical records relating to success of implantation, pregnancy rate, or the like. The said patient medical record database may be located within a dedicated facility or available from an external source (e.g., crowdsource, public database, etc.), accessible via a communication network. The AI Engine 1202 can also receive one or more inputs of one or more data or dataset generated by one or more CNN disclosed within the present disclosure, stored on cloud-based server 1214. The said cloud server and services are commonly referred to as "cloud computing", "on-demand computing", "software as a service (SaaS)", "platform computing", "network-accessible platform", "cloud services", "data centers," and the like. The term "cloud" can include a collection of hardware and software that forms a shared pool of configurable computing resources (e.g., networks, servers, storage, applications, services, etc.), which can be suitably provisioned to provide on-demand self-service, network access, resource pooling, elasticity and measured service, among other features. The AI Engine 1202 comprises one or more computing architecture, hardware, software, known to one of ordinary skill in the art, to enable it to execute one or more instructions or algorithms as to process one or more external inputs. One or more processed dataset or analysis or prediction or clinical insights generated by AI Engine 1202 may be sent and stored on cloud-based server 1214 for distribution. In various embodiments, cloud-based server 1214 comprises one or one or more software application (or desktop client) 1216 to enable the development of one or more software application product (or mobile client) 1218 providing one or more functions, including but not limited to, data processing, data analysis, data presentation in graphical form, data annotation, or the like. In various embodiments, the application product comprises a system and methods for collecting, processing, and synthesizing clinical insights from at least one patient data, US image from a US scanner/device, retrieved US image, patient medical record from an electronic medical record database, outcomes data, patient record relating to fertility, patient endocrinology record, patient clinical notes, physician clinical notes, data from database residing on said cloud-based server, results from one or more output layer of one or more said ANNs, artificial intelligence engine. In various embodiments, at least one application enables the retrieval or distribution of one or more clinical insights. Clinical insights may include a variety of reproductive endocrinology insights such as expected patient egg retrieval volume, recommended timing of egg retrieval, quantity of eggs to anticipate per patient and per day, anticipated maturity date of eggs, anticipated embryo number, anticipated embryo quality, quantity and scheduling of embryo biopsies, patient care planning, reduction of error rates and improvement of pregnancy rates. In various embodiments, a user (e.g., physician) may access the clinical insights from a desktop client 1216. Similarly, a patient may access the clinical insights from a mobile client 1218, or vice versa. In one implementation, mobile client 1218 comprises one or mobile app product 1220 capable of communicating with cloud-server 1214 via a communication network 1222 to access said information. Similarly, desktop client 1216 can access cloud-based server 1214 via communication network 1222. In various embodiments, communication network 1222 comprises, but is not limited to, one or more; LAN, WAN, wireless network, cellular network, Internet, the like, or combinations thereof.

Figure 13:
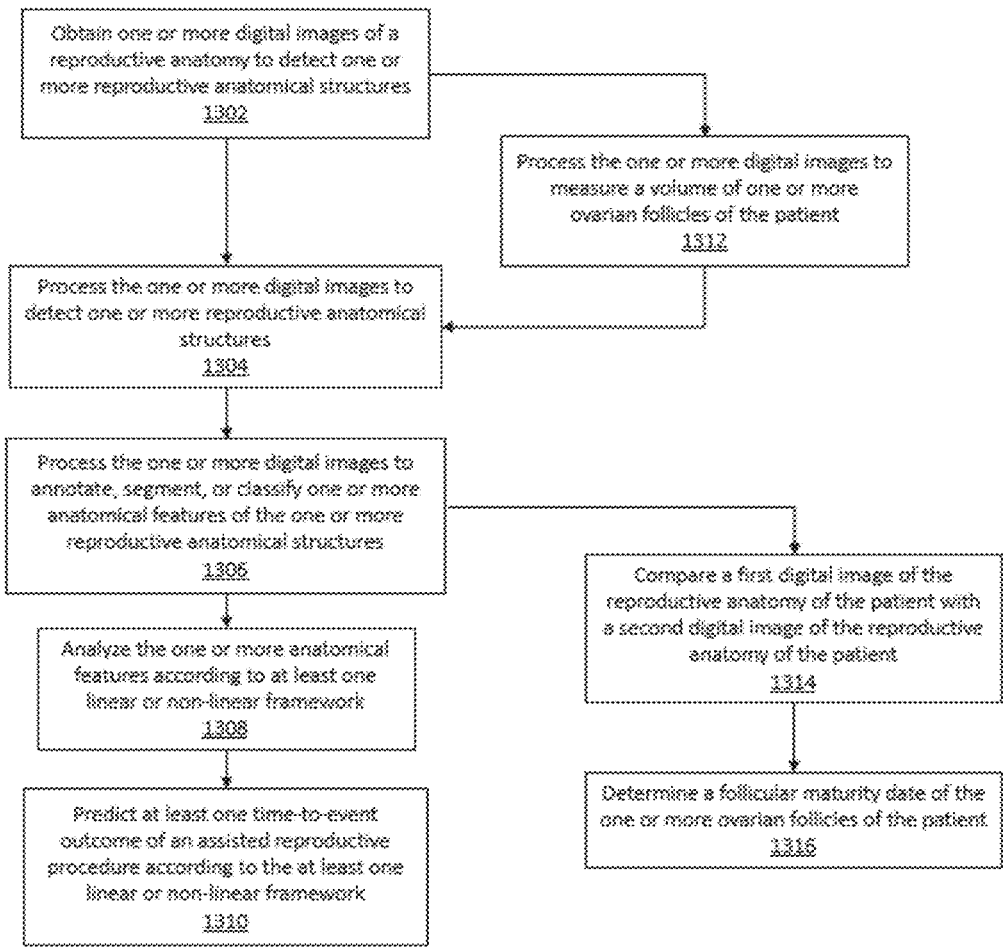
FIG. 13 is a process flow diagram of a method for determining a follicular maturity date of an ovarian follicle, in accordance with an embodiment of the present disclosure.

Referring to FIG. 13, a process flow diagram for determining a follicular maturity date of an ovarian follicle is shown, according to various embodiments. In step 1302, one or more digital images of a reproductive anatomy is obtained to detect one or more reproductive anatomical structures. In step 1304, the said digital images are processed to detect one or more reproductive anatomy structures. In step 1306, the one or more digital images are processed to annotate, segment, or classify one or more anatomical features of the one or more reproductive anatomical structures. In step 1308, the one or more anatomical features are analyzed according to at least one linear or non-linear framework. In step 1310, at least one time-to-event outcome of an assisted reproductive procedure is predicted according to the at least one linear or non-linear framework. In an alternative step 1312, the one or more digital images are processed to measure a volume of one or more ovarian follicles of the patient whereby the output provides an additional input to step 1304. In another alternative step 1314, an output of step 1306 provides an input for the comparison of a first digital image of the reproductive anatomy of the patient with a second digital image of the reproductive anatomy of the patient to provide an output. In step 1316, the output of step 1314 serves as input to determine a follicular maturity date of the one or more ovarian follicles of the patient.

Figure 14:
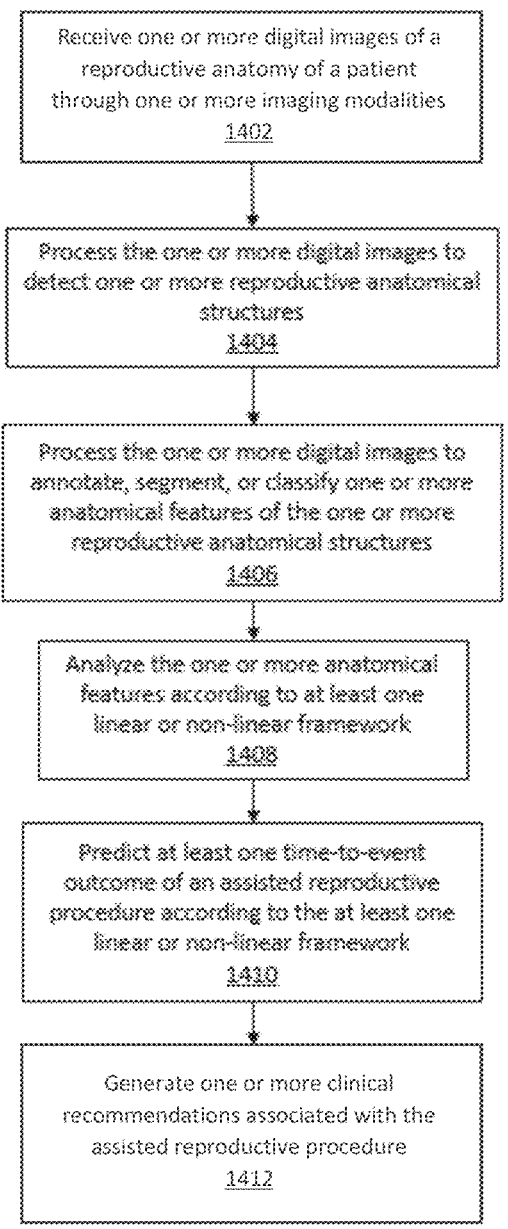
FIG. 14 is a process flow diagram of a method for generating a clinical recommendation, in accordance with an embodiment of the present disclosure; and, FIG. 15 is a process flow diagram of a method for generating a clinical recommendation associated, in accordance with an embodiment of the present disclosure.

Referring to FIG. 14, a process flow diagram of a process for generating a clinical recommendation associated with the assisted reproductive procedure is shown, according to various embodiments. In step 1402, one or more digital images of a patient's reproductive anatomy is received through one or more imaging modalities. In step 1404, the one or more digital images are processed to detect one or more reproductive anatomical structures. In step 1406, the one or more digital images are processed to annotate, segment, or classify one or more anatomical features of the one or more reproductive anatomical structures. In step 1408, the one or more anatomical structures are analyzed according to at least one linear or non-linear framework. In step 1410, at least one time-to-event outcome of an assisted reproductive procedure is predicted according to at least one linear or non-linear framework. In step 1412, clinical recommendations associated with the assistive reproductive procedure are generated by the process.

Figure 15:
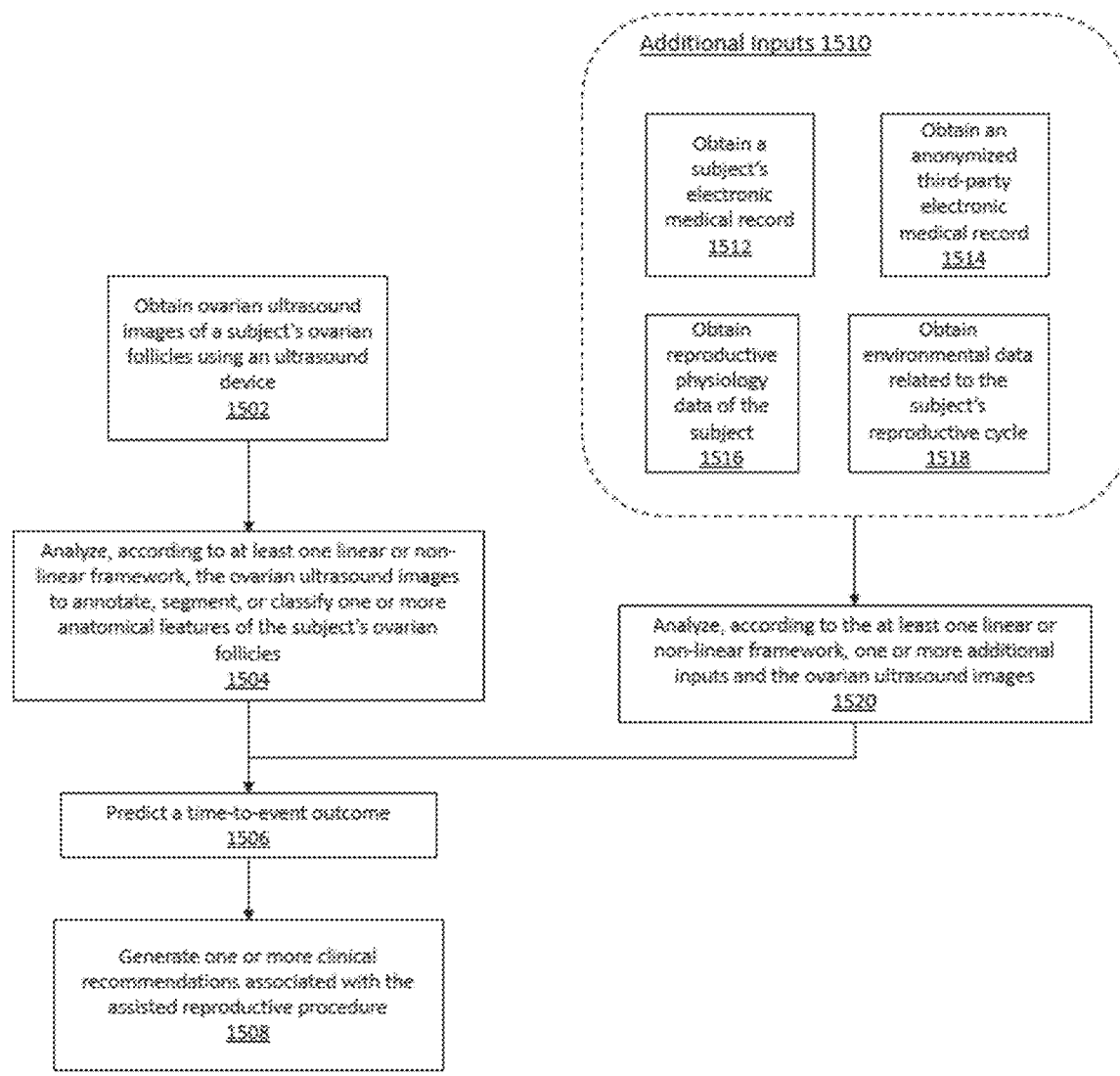

Referring to FIG. 15, a process flow diagram of a process for generating a clinical recommendation associated with the assisted reproductive procedure is shown, according to various embodiments. In step 1502, ultrasound images of a subject's ovarian follicles are obtained using an ultrasound device. In step 1504, the ovarian ultrasound images are analyzed, according to at least one linear or non-linear framework, to annotate, segment, or classify one or more anatomical features of the subject's ovarian follicles. In step 1506, a time-to-event outcome is predicted and subsequently in step 1508, one or more clinical recommendations associated with the assisted reproductive procedure is generated by the process. In another embodiment, addition inputs 1510 are obtained through one or more processes. In step 1512, a subject's electronic medical record is obtained as an input. In step 1514, an anonymized third-party electronic medical record is obtained as an input. In step 1516, a reproductive physiology data of the subject is obtained as an input. In step 1518, an environmental data related to the subject's reproductive cycle is obtained as an input. In step 1520, these additional inputs 1510 are analyzed, according to at least one linear or non-linear framework, together with the ovarian ultrasound images, to predict a time-to-event outcome in step 1506, and subsequently in step 1508, to generate one or more clinical recommendations associated with the assisted reproductive procedure.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention. The terms and expressions which have been employed in the foregoing description are used therein as terms of description and not of limitation, and there is no intention in the use of such terms and expressions to exclude equivalents of the features shown and described or portions thereof, it being recognized that the scope of the invention is defined and limited only by the claims which follow.

What is claimed is:

1. A computer-aided diagnostic and predictive image processing system for the clinical management of infertility through assisted reproductive technology, the system comprising:
   an imaging sensor operable to execute a three-dimensional (3D) ultrasound to collect one or more 3D images of a reproductive anatomy of a patient;
   a storage device for storing, locally or remotely, the one or more 3D images of the reproductive anatomy of the patient; and
   at least one processor operably engaged with at least one computer-readable storage medium storing computer-executable instructions thereon that, when executed, cause the processor to perform one or more actions, the one or more actions comprising:
      receiving the one or more 3D images of the reproductive anatomy of the patient;
      processing the one or more 3D images of the reproductive anatomy of the patient to detect one or more reproductive anatomical structures and annotate one or more anatomical features of the one or more reproductive anatomical structures;
      analyzing the one or more anatomical features according to at least one non-linear framework to predict at least one time-to-event outcome, wherein the at least one non-linear framework comprises an artificial neural network selected from a convolutional neural network and a fully convolutional neural network and the at least one time-to-event outcome comprises an egg retrieval date from the patient for in vitro fertilization; and
      generating at least one graphical user output in response to the at least one time-to-event outcome prediction, the at least one graphical user output corresponding to one or more recommended clinical actions for the clinical management of infertility in the patient.

2. The system of claim 1 wherein the one or more actions of the processor further comprise receiving a health record of the patient from an electronic health record database and analyzing the health record of the patient, together with the one or more anatomical features, according to the at least one non-linear framework to predict the at least one time-to-event outcome, wherein the health record of the patient comprises one or more selected from the group consisting of diagnostic results, body fluid biomarkers, hormone markers, hormone levels, genomic biomarkers, proteomic biomarkers, therapeutic treatments, treatment schedule, implantation schedule, follicle size and number, follicle growth rate, pregnancy rate, and date of implantation.

3. The system of claim 2 wherein the one or more actions of the processor further comprise receiving a health record of an anonymized patient undergoing infertility treatment from an electronic health record database and analyzing the health record of the anonymized patient, together with the one or more anatomical features, according to the at least one non-linear framework to predict the at least one time-to-event outcome, wherein the health record of the anonymized patient undergoing infertility treatment comprises one or more selected from the group consisting of ultrasound images, images of the reproductive anatomy, diagnostic results, body fluid biomarkers, hormone markers, hormone levels, genomic biomarkers, proteomic biomarkers, therapeutic treatments, treatment schedule, implantation schedule, follicle size and number, follicle growth rate, follicle growth rate, pregnancy rate, and date of implantation.

4. The system of claim 1 wherein the one or more actions of the processor further comprise:
   receiving clinical outcomes data related to the patient;
   storing the clinical outcomes data related to the patient in an outcome database; and
   analyzing the clinical outcomes data related to the patient, together with the one or more anatomical features, according to the at least one non-linear framework to predict the at least one time-to-event outcome.

5. The system of claim 1 wherein the at least one non-linear framework comprises a fully convolutional neural network comprising a plurality of convolution layers.

6. The system of claim 1 wherein the one or more actions of the processor further comprise receiving reproductive physiology data of the patient and analyzing the reproductive physiology data associated with the patient, together with the one or more anatomical features, according to the at least one non-linear framework to predict the at least one time-to-event outcome.

7. The system of claim 1 wherein the one or more actions of the processor further comprise receiving environmental data related to a reproductive cycle of the patient and analyzing the environmental data, together with the one or more anatomical features, according to the at least one non-linear framework to predict the at least one time-to-event outcome, wherein the environmental data comprises longitudinal medical record data of the patient collected based on one or more selected from the group consisting of: day of reproductive cycle, time of day, and time of week.

8. The system of claim 5 wherein the reproductive anatomy of the patient comprises the anatomy of the patient's follicles, and the fully convolutional neural network is configured to segment the follicles based on quality and/or changes in quantity.

9. The system of claim 1, wherein the one or more actions further comprise:
receiving reproductive physiology data associated with the patient and environmental data related to the reproductive cycle of the patient; and
together with the one or more anatomical features, analyzing the reproductive physiology data and the environmental data according to the at least one non-linear framework to predict the at least one time-to-event outcome,
wherein:
the reproductive physiology data of the patient comprises one or more selected from the group consisting of: diagnostic results, diagnostic biomarkers, genomic markers, proteomic marker, body fluid analytes, chemical panels, and measured hormone levels; and
the environmental data comprises longitudinal medical record data collected from the patient based on one or more selected from the group consisting of: day of reproductive cycle, time of day, and time of week.

10. The system of claim 9, wherein:
the at least one non-linear framework comprises a survival convolution neural network; and
the one or more actions further comprise
obtaining one or more patient phenotype from a longitudinal medical record of the patient, and
analyzing the one or more patient phenotype, together with the one or more anatomical features, the reproductive physiology data and the environmental data, according to the survival convolution neural network to predict the at least one time-to-event outcome.

11. A computer-aided diagnostic and predictive image processing system for the clinical management of infertility through assisted reproductive technology, the system comprising:
an imaging sensor operable to execute one or more imaging modalities to collect one or more digital images of a reproductive anatomy of a patient, wherein the one or more imaging modalities comprise a three-dimensional (3D) ultrasound, the one or more digital images comprise one or more 3D ultrasound images, and the reproductive anatomy comprises an ovarian anatomy of the patient;
an artificial intelligence engine configured to receive, locally or remotely, the one or more digital images of the reproductive anatomy of the patient, and to process the one or more digital images of the reproductive anatomy of the patient and to generate at least one time-to-event outcome prediction according to at least one non-linear framework, wherein the at least one non-linear framework is selected from the group consisting of a convolutional neural network, a recurrent neural network, a fully convolutional neural network, a dilated residual network, a generative adversarial network and combinations thereof, and the at least one time-to-event outcome prediction comprises an optimal egg retrieval date for in vitro fertilization;
an electronic medical record database comprising one or more longitudinal medical records of one or more patients undergoing infertility treatment with assisted reproductive technology, the electronic medical record database being configured to communicate medical record data of the one or more patients undergoing infertility treatment with assisted reproductive technology to the artificial intelligence engine such that the medical record data is incorporated into the at least one non-linear framework;
an outcome database comprising one or more longitudinal records of clinical outcomes of one or more patients undergoing infertility treatment with assisted reproductive technology, the outcome database being configured to communicate clinical outcomes data of the one or more patients undergoing infertility treatment with assisted reproductive technology to the artificial intelligence engine such that the clinical outcomes data is incorporated into the at least one non-linear framework, wherein the clinical outcomes data relates to a success rate of embryo implantation and pregnancy following in vitro fertilization;
an application server operably engaged with the artificial intelligence engine to receive the one or more 3D digital images of the reproductive anatomy of the patient, the medical record data, the outcomes data, and the at least one time-to-event outcome prediction, the application server executing an application configured to generate one or more recommended clinical actions for the clinical management of infertility through assisted reproductive technology in response to the at least one time-to-event outcome prediction, the one or more recommended clinical actions comprising a recommended time of egg retrieval from the patient; and
a user device communicably engaged with the application server, the user device being configured to display a graphical user interface containing the one or more recommended clinical actions for the clinical management of infertility.

12. The system of claim 11 wherein the user device is a smart phone.

13. The system of claim 11 wherein the application server is configured to communicate anonymized patient historical data of one or more patients undergoing infertility treatment with assisted reproductive technology to the artificial intelligence engine, the anonymized patient historical data being incorporated into the at least one non-linear framework.

14. The system of claim 11, wherein the at least one non-linear framework comprises one or more convolutional neural networks optimized with multi-task learning.

15. A computer-readable storage medium encoded with computer-executable instructions for commanding one or more processors to execute operations of a method for predicting at least one time-to-event outcome based on one or more ultrasound images of a reproductive anatomy of a patient and one or more patient phenotypes obtained from a patient medical record, the operations comprising:
receiving one or more ultrasound images of a reproductive anatomy of a patient;
receiving one or more patient medical records from an electronic medical record database, the one or more patient medical records comprising stored longitudinal medical records of one or more patients undergoing infertility treatment through assisted reproductive technology;
processing the one or more ultrasound images of the reproductive anatomy of the patient to detect one or more reproductive anatomical structures and annotate one or more anatomical features of the one or more reproductive anatomical structures;

processing the patient medical record of the one or more patients undergoing infertility treatment through assisted reproductive technology to identify one or more patient phenotypes, the one or more patient phenotypes being selected from the group consisting of ovulation, anovulation, oligo ovulation, endometriosis, male factor infertility, tubal factor infertility, and decreased ovarian reserve;

analyzing the one or more anatomical features and the one or more patient phenotypes according to at least one non-linear framework, the non-linear framework comprising a convolutional neural network; and predicting the at least one time-to-event outcome according to the at least one non-linear framework, the at least one time-to-event outcome prediction comprising an optimal egg retrieval date from the patient for in vitro fertilization.

16. The computer-readable storage medium of claim 15, the operations further comprising analyzing historical outcome data of one or more patients undergoing infertility treatment, together with the one or more anatomical features and the one or more patient phenotypes, according to the at least one non-linear framework to predict the at least one time-to-event outcome.

17. The computer-readable storage medium of claim 15, the operations further comprising generating one or more reproductive endocrinology insights in response to the at least one time-to-event outcome, wherein the one or more reproductive endocrinology insights are selected from the group consisting of: expected egg retrieval volume from the patient; recommended timing of egg retrieval from the patient; daily quantity of eggs anticipated from the patient; anticipated maturity date of the patient's eggs; anticipated number of embryos of the patient; anticipated quality of the patient's embryos; quantity and scheduling of embryo biopsies; and improvement of pregnancy rates.

18. The computer-readable storage medium of claim 15, the operations further comprising receiving reproductive physiology data of the patient and analyzing the reproductive physiology data, together with the one or more anatomical features and the one or more patient phenotypes, according to the at least one non-linear framework to predict the at least one time-to-event outcome, wherein the reproductive physiology data of the patient comprises one or more of a diagnostic result, biomarker, genomic marker, proteomic marker, body fluid analyte, chemical panel, and measured hormone level.

19. The computer-readable storage medium of claim 15, wherein the one or more ultrasound images of the reproductive anatomy of the patient comprise a three-dimensional (3D) ultrasound image.

20. The computer-readable storage medium of claim 15, wherein the at least one non-linear framework comprises a plurality of convolutional neural networks.

* * * * *